United States Patent
Marchionni et al.

(10) Patent No.: US 9,776,983 B2
(45) Date of Patent: Oct. 3, 2017

(54) METHOD FOR MANUFACTURING FLUOROPOLYMERS

(71) Applicant: SOLVAY SOLEXIS S.p.A., Bollate (IT)

(72) Inventors: Giuseppe Marchionni, Milan (IT); Vito Tortelli, Milan (IT); Ivan Wlassics, Garessio (IT); Valeriy Kapelyushko, Alessandria (IT)

(73) Assignee: SOLVAY SOLEXIS S.P.A., Bollate (IT)

( * ) Notice: Subject to any disclaimer, the term of this patent is extended or adjusted under 35 U.S.C. 154(b) by 465 days.

(21) Appl. No.: 14/198,443

(22) Filed: Mar. 5, 2014

(65) Prior Publication Data
US 2014/0228531 A1   Aug. 14, 2014

Related U.S. Application Data

(62) Division of application No. 13/002,781, filed as application No. PCT/EP2009/058530 on Jul. 6, 2009, now Pat. No. 8,703,889.

(30) Foreign Application Priority Data

Jul. 8, 2008 (EP) .................... 08159936
Nov. 3, 2008 (EP) .................... 08168221

(51) Int. Cl.
*C08F 14/26* (2006.01)
*C07D 317/34* (2006.01)
(Continued)

(52) U.S. Cl.
CPC ......... *C07D 317/34* (2013.01); *C07D 317/42* (2013.01); *C08F 14/18* (2013.01); *C08F 114/26* (2013.01)

(58) Field of Classification Search
USPC .................. 526/204, 144; 549/449
See application file for complete search history.

(56) References Cited

U.S. PATENT DOCUMENTS 3,271,341 A * 9/1966 Garrison, Jr. ......... C07C 59/135
                                                    524/773
3,282,875 A * 11/1966 Connolly .............. C07C 309/82
                                                    524/795
(Continued)

FOREIGN PATENT DOCUMENTS

EP     1 155 055 B1     4/2003
EP     1155055 B1  *    4/2003
(Continued)

OTHER PUBLICATIONS

Chambers R. D., "Fluorine in Organic Chemistry," 2004, Oxford (UK) Blackwell Publishing, Ltd., CRC Press, ISBN 0-8493-1790-8 (USA & Canada), p. 198-199; 4 pgs.

*Primary Examiner* — Mark Kaucher
*Assistant Examiner* — Henry Hu
(74) *Attorney, Agent, or Firm* — Arent Fox LLP

(57) ABSTRACT

The invention pertains to a method for making a fluoropolymer comprising an aqueous emulsion polymerization of one or more fluorinated monomers wherein said aqueous emulsion polymerization is carried out in the presence of at least one cyclic fluorocompound of the following formula (I):

(Continued)

wherein $X_1$, $X_2$, $X_3$, equal or different from each other are independently selected among H, F, and $C_{1-6}$ (per)fluoroalkyl groups, optionally comprising one or more catenary or non-catenary oxygen atoms; L represents a bond or a divalent group; $R_F$ is a divalent fluorinated $C_{1-3}$ bridging group; Y is a hydrophilic function selected among anionic functionalities, cationic functionalities and non-ionic functionalities.

4 Claims, 5 Drawing Sheets

(51) Int. Cl.
*C07D 317/42* (2006.01)
*C08F 14/18* (2006.01)
*C08F 114/26* (2006.01)

(56) References Cited

U.S. PATENT DOCUMENTS

| | | |
|---|---|---|
| 4,369,266 A | 1/1983 | Kuhls et al. |
| 5,285,002 A | 2/1994 | Grootaert |
| 6,586,626 B2 * | 7/2003 | Okazoe ............... C07B 39/00 560/125 |
| 7,429,428 B2 * | 9/2008 | Watakabe ............ C08F 214/18 429/314 |
| 8,703,889 B2 * | 4/2014 | Marchionni ......... C07D 317/42 526/144 |
| 2005/0113507 A1 | 5/2005 | Bladel et al. |
| 2007/0015864 A1 * | 1/2007 | Hintzer ............... C08L 27/12 524/544 |
| 2007/0015865 A1 | 1/2007 | Hintzer et al. |
| 2007/0015866 A1 | 1/2007 | Hintzer et al. |
| 2007/0025902 A1 | 2/2007 | Hintzer et al. |
| 2007/0276103 A1 | 11/2007 | Guerra et al. |

FOREIGN PATENT DOCUMENTS

| | | |
|---|---|---|
| EP | 1 676 867 A1 | 7/2006 |
| EP | 1 676 868 A1 | 7/2006 |
| EP | 1676867 A1 * | 7/2006 |
| EP | 1676868 A1 * | 7/2006 |
| EP | 2 143 738 A1 | 1/2010 |
| EP | 2143738 A1 * | 1/2010 |
| WO | WO-2004-088422 A1 * | 10/2004 |
| WO | WO 2004/088422 A1 | 10/2004 |
| WO | WO-2010-003929 A1 * | 1/2010 |
| WO | WO 2010/003929 A1 | 1/2010 |

* cited by examiner

METHOD FOR MANUFACTURING FLUOROPOLYMERS

CROSS-REFERENCE TO RELATED CASES

This application is a Divisional of U.S. patent application Ser. No. 13/002,781, filed Mar. 14, 2011, which is a National Stage entry of International Patent Application No. PCT/EP09/58530, filed Jul. 6, 2009, which claims the benefit of priority from European Application No. 08159936.7, filed Jul. 8, 2008 and European Application No. 08168221.3, filed Nov. 3, 2008, each of which is hereby incorporated by reference in their entirety.

TECHNICAL FIELD

The present invention pertains to a method of making fluoropolymer dispersions, to fluoropolymer dispersions therefrom and to cyclic fluorosurfactants useful in said method.

BACKGROUND ART

Fluoropolymers, i.e. polymers having a fluorinated backbone, have been long known and have been used in a variety of applications because of several desirable properties such as heat resistance, chemical resistance, weatherability, UV-stability etc.

A frequently used method for producing fluoropolymers involves aqueous emulsion polymerization of one or more fluorinated monomers generally involving the use of fluorinated surfactants. Frequently used fluorinated surfactants include perfluorooctanoic acids and salts thereof, in particular ammonium perfluorooctanoic acid.

Recently, perfluoroalkanoic acids having 8 or more carbon atoms have raised environmental concerns. For instance, perfluoroalkanoic acids have been found to show bioaccumulation. Accordingly, efforts are now devoted to phasing out from such compounds and methods have been developed to manufacture fluoropolymer products using alternative surfactants having a more favourable toxicological profile.

Several approaches have been recently pursued to this aim, typically involving fluorosurfactants comprising a perfluoroalkyl chain interrupted by one or more catenary oxygen atoms, said chain having an ionic carboxylate group at one of its ends.

Examples of these compounds which are endowed with improved bioaccumulation profile over perfluoro alkanoic acids having 8 or more carbon atoms can be found notably in US 2007276103 (3M INNOVATIVE PROPERTIES CO) 29, Nov. 2007, US 2007015864 (3M INNOVATIVE PROPERTIES CO) 18, Jan. 2007, US 2007015865 (3M INNOVATIVE PROPERTIES CO) 18, Jan. 2007, US 2007015866 (3M INNOVATIVE PROPERTIES CO) 18, Jan. 2007.

It would thus be desirable to find alternative fluorinated surfactants that can be used in the emulsion polymerization of fluorinated monomers which desirably show lower bioaccumulation/biopersistence than perfluoro alkanoic acids having 8 or more carbon atoms.

It would further be desirable that the surfactant properties of said alternative fluorinated surfactants be such that polymerization can be carried out in a convenient and cost effective way, using equipment commonly used in the aqueous emulsion polymerization of fluorinated monomers with traditional surfactants.

SUMMARY OF THE INVENTION

It has been found that cyclic fluorocompounds of the following formula (I):

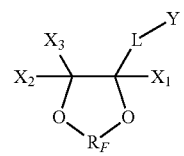

(I)

as detailed below, are effective in the aqueous emulsion polymerization, even when used without the addition of other surfactants such as perfluoroalkanoic acids and salts thereof.

Moreover, the Applicant has surprisingly found that above mentioned cyclic fluorocompounds (I) have significantly improved biopersistence behaviour over perfluoroalkanoic acids derivatives, so that their toxicological profile is much improved.

Finally, these cyclic fluorocompounds (I) have a higher volatility over perfluoroalkanoic acids derivatives, so that their residues in final parts obtained from fluoropolymer dispersions containing the same can be significantly reduced.

Thus, in one aspect, the invention relates to a method for making a fluoropolymer comprising an aqueous emulsion polymerization of one or more fluorinated monomers wherein said aqueous emulsion polymerization is carried out in the presence of at least one cyclic fluorocompound of the following formula (I):

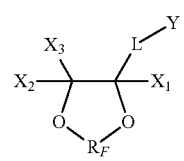

(I)

wherein $X_1$, $X_2$, $X_3$, equal to or different from each other are independently selected among H, F, and $C_{1-6}$ (per)fluoroalkyl groups, optionally comprising one or more catenary or non-catenary oxygen atoms; L represents a bond or a divalent group; $R_F$ is a divalent fluorinated $C_{1-3}$ bridging group; Y is a hydrophilic function selected among anionic functionalities, cationic functionalities and non-ionic functionalities.

The hydrophilic function Y can be notably selected among non-ionic functions of formulae —$(OR_H)_n$—OH, wherein $R_H$ is a divalent hydrocarbon group, and n is an integer of 1 to 15.

As an alternative, the hydrophilic function Y can be notably selected among cationic functions of formulae:

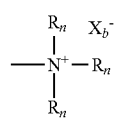

(1)

-continued

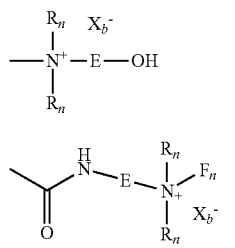
(2)

(3)

wherein $R_n$, equal or different at each occurrence, represents a hydrogen atom or a $C_{1-6}$ hydrocarbon group (preferably an alkyl group), E is a $C_{1-3}$ divalent hydrocarbon group and $X_b^-$ is an anion selected among $OH^-$, $Cl^-$, $Br—$, $I^-$.

Nevertheless, the hydrophilic function Y is preferably selected among anionic functions, in particular among those of formulae:

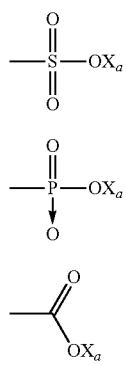
(1″)

(2″)

(3″)

wherein $X_a$ is H, a monovalent metal (preferably an alkaline metal) or an ammonium group of formula $—N(R'_n)_4$, wherein R'n, equal or different at each occurrence, represents a hydrogen atom or a $C_{1-6}$ hydrocarbon group (preferably an alkyl group).

Most preferably, hydrophilic function Y is a carboxylate of formula (3″), as above detailed.

BRIEF DESCRIPTION OF THE DRAWINGS

For a detailed description of the preferred embodiments of the invention, reference will now be made to the accompanying drawings in which.

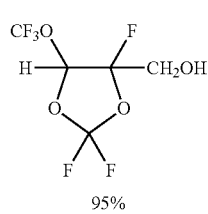
(B)

95%

Figure 2:
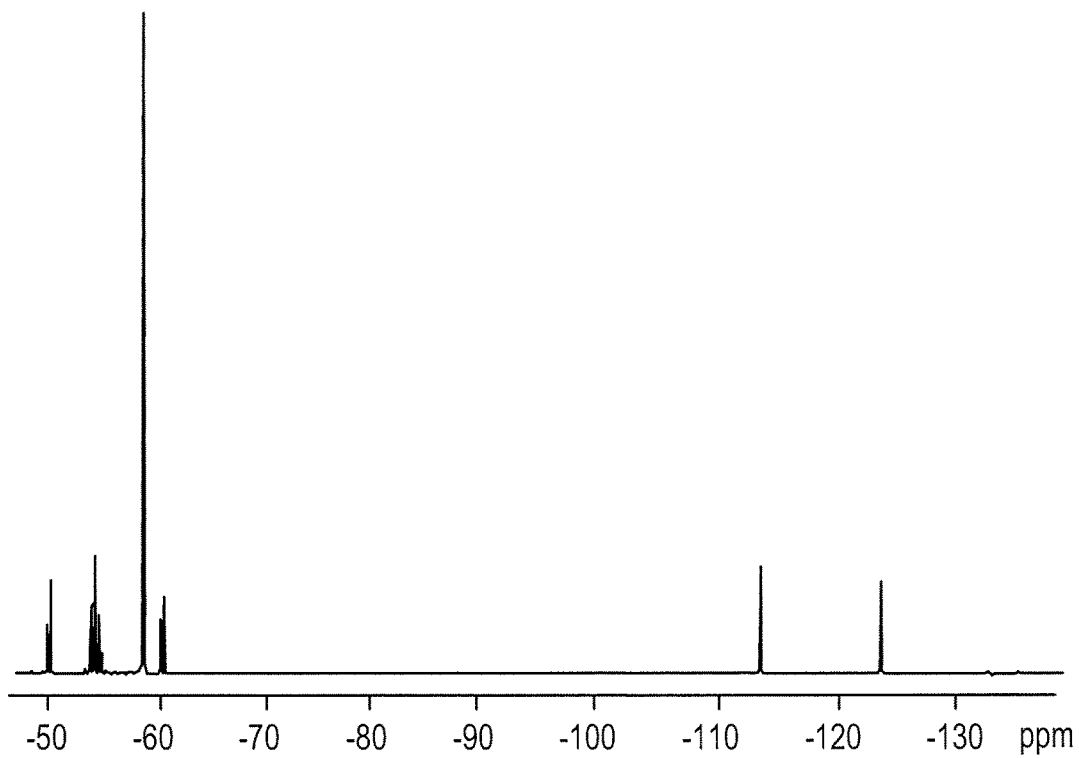

FIG. 2 depicts the $^{19}$F-NMR spectrum of compound (E);

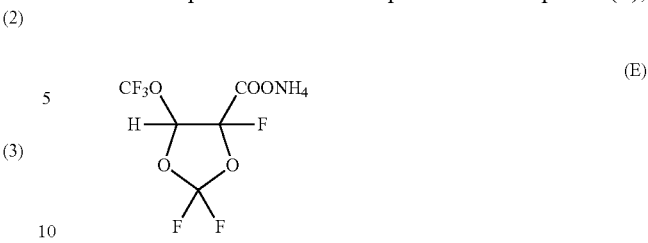
(E)

Figure 3:
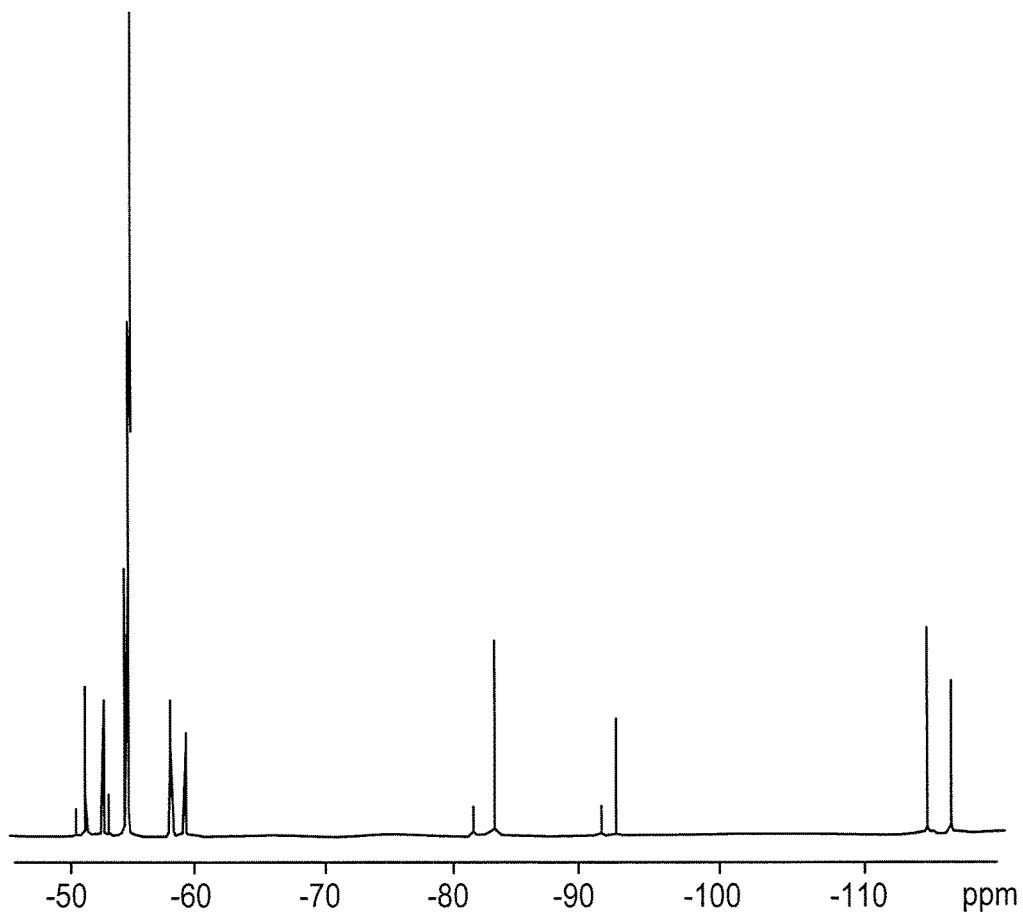

FIG. 3 depicts the $^{19}$F-NMR spectrum recorded on compound (H);

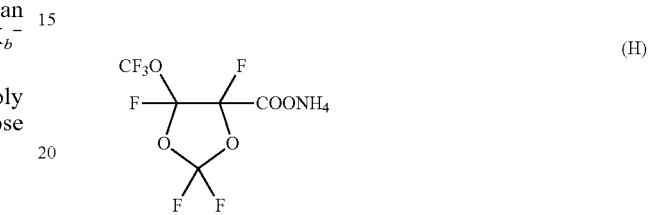
(H)

Figure 4:
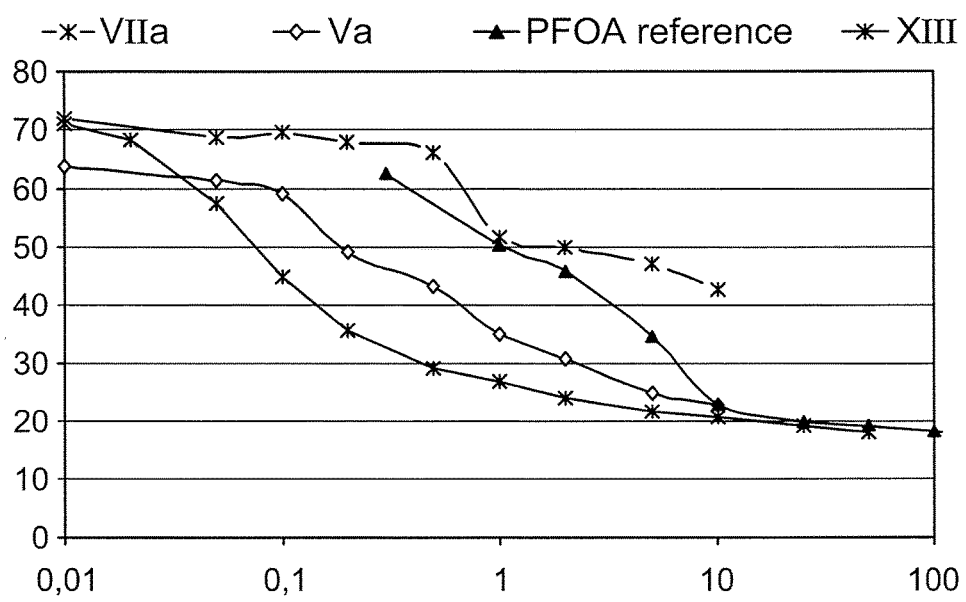
Figure 5:
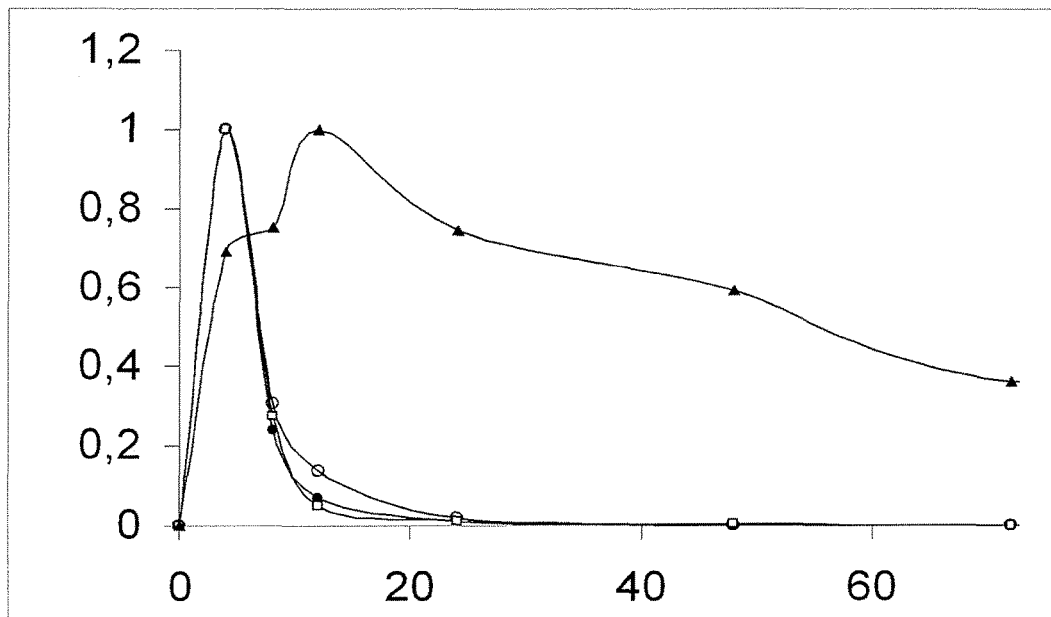

FIG. 4 illustrates a sketch of the surface tension (in mN/m) as a function of concentration (in g/l) for compounds Va (with $X_a$=$NH_4$), VIIa (with $X_a$=$NH_4$) and ammonium perfluorooctanoate (APFO);

FIG. 5 illustrates plasma concentrations for compound VIIa ($X_a$=$NH_4$), Va ($X_a$=$NH_4$), XIII ($X_a$=$NH_4$) and APFO as a function of time;

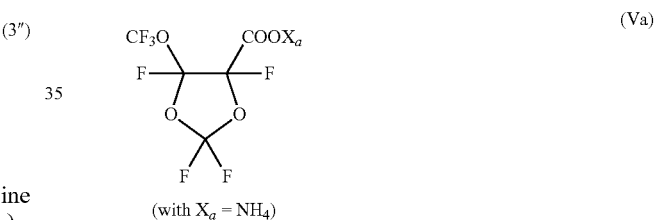
(Va)
(with $X_a$ = $NH_4$)

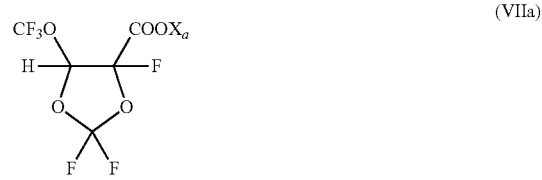
(VIIa)
(with $X_a$ = $NH_4$)

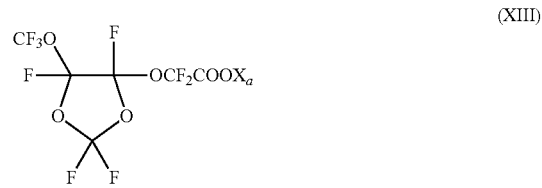
(XIII)
(with $X_a$ = $NH_4$)

Figure 6:
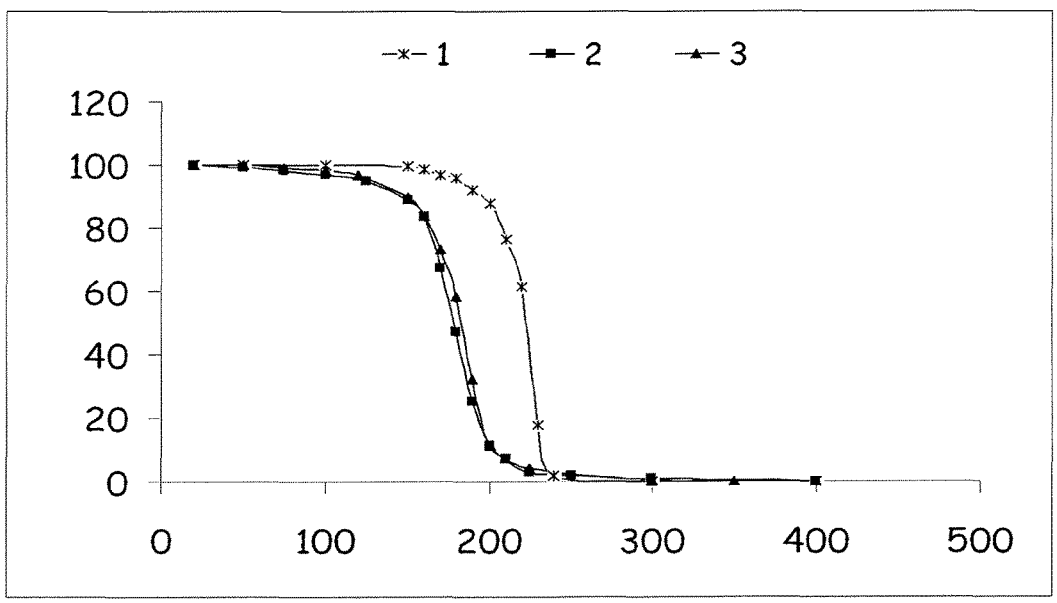
Figure 7:
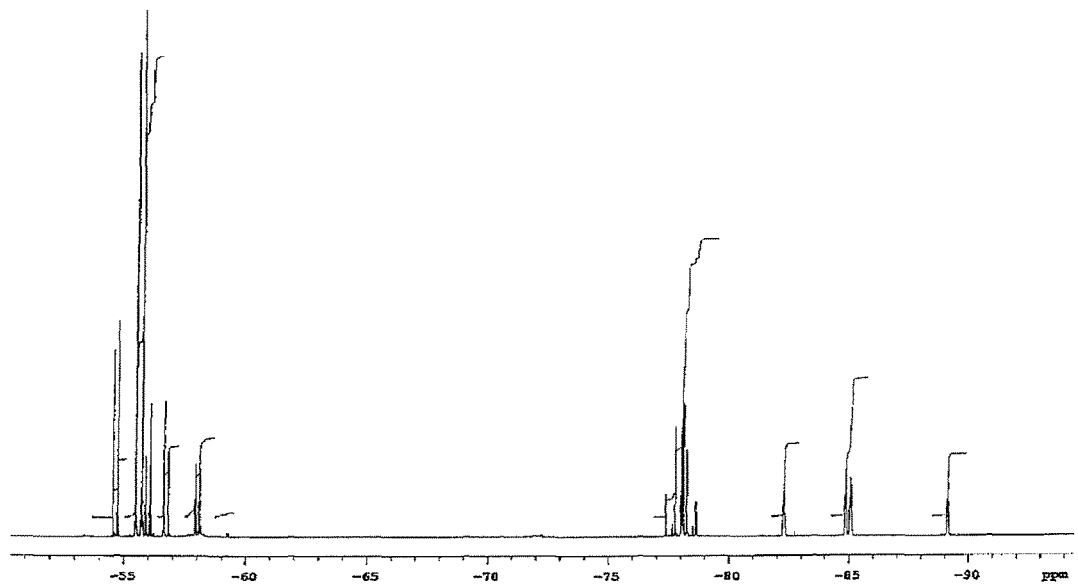
Figure 8:
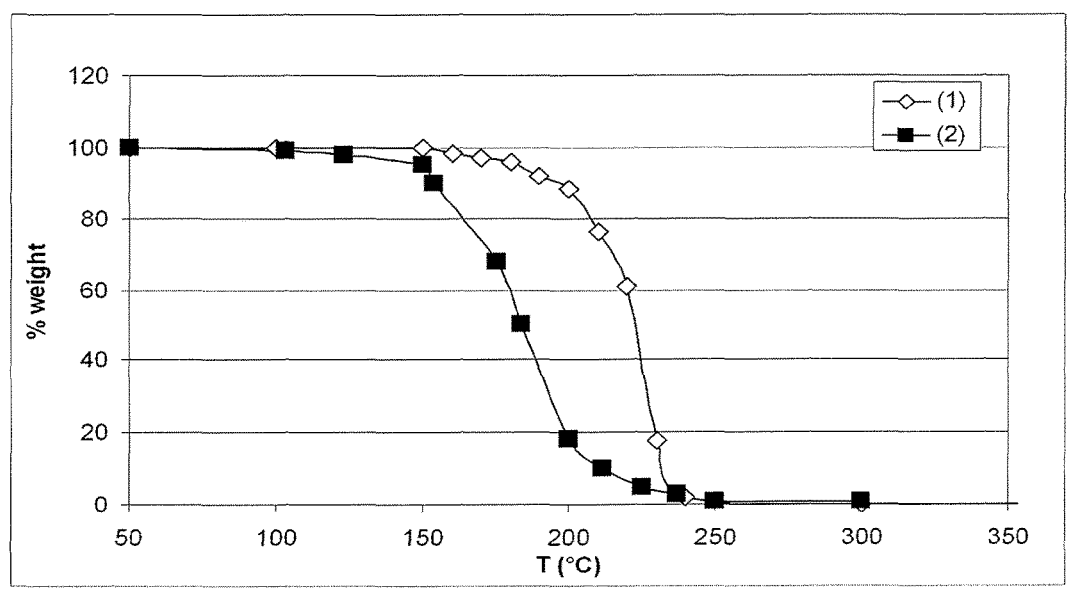
Figure 9:
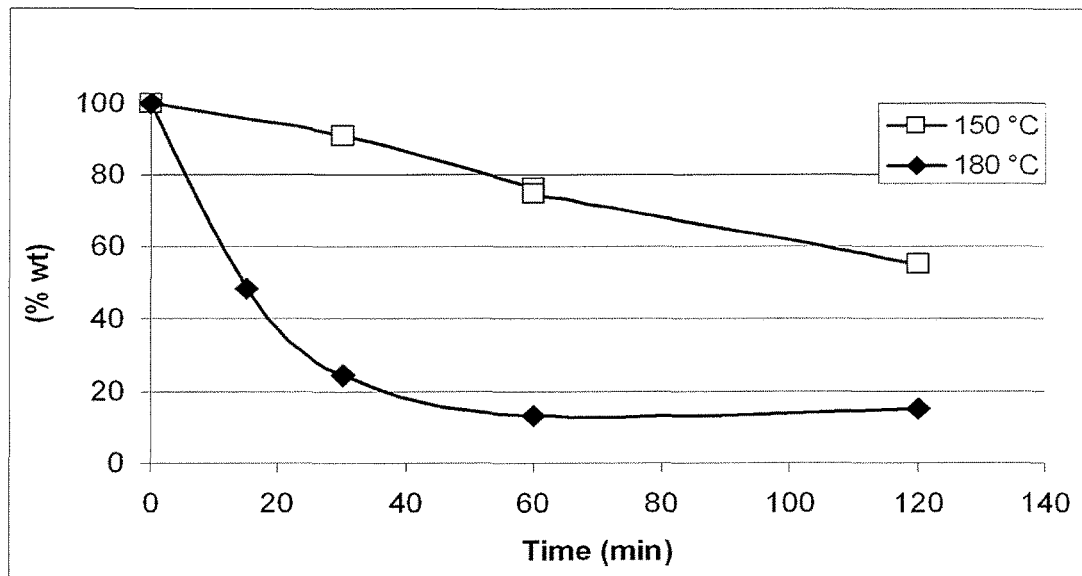

FIG. 6 depicts the thermogravimetric analysis (TGA) traces as % weight loss as a function of temperature (in ° C.) for APFO (1), compound Va ($X_a$=$NH_4$) (2) and VIIa ($X_a$=$NH_4$) (3);

FIG. 7 depicts the $^{19}$F-NMR spectrum recorded on ammonium salt (compound XIII, with $X_a$=$NH_4$);

FIG. 8 depicts the thermogravimetric analysis (TGA) traces as % weight loss as a function of temperature (in ° C.) for APFO (1) and compound XIII ($X_a$=$NH_4$) (2); and FIG. 9 provides TGA isothermal scans under vacuum carried out on compound XIII ($X_a=NH_4$) at T=150° C. and 180° C.

DETAILED DESCRIPTION

According to a first embodiment of the invention, the cyclic fluorocompound complies with formula (II) here below:

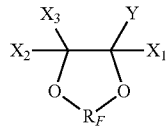
(II)

wherein $X_1$, $X_2$, $X_3$, Y and $R_F$ have the same meaning as above defined.

More preferably, the cyclic fluorocompound complies with formula (III) here below:

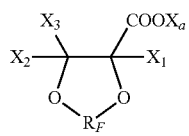
(III)

wherein $R_F$, $X_1$, $X_2$, $X_3$, and $X_a$ have the same meaning as above defined.

According to a first variant of this preferred embodiment, the cyclic fluorocompound complies with formula (IV):

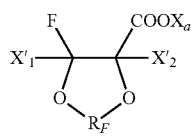
(IV)

wherein $X'_1$ and $X'_2$, equal to or different from each other, are independently a fluorine atom, a —$R'_f$ group or —$OR'_f$ group, wherein $R'_f$ is a $C_{1-3}$ perfluoroalkyl group, preferably with the provision that at least one of $X'_1$ and $X'_2$ are different from fluorine, and $R_F$ and $X_a$ have the same meanings as above defined.

Compounds of formula (IV) can be notably obtained by reaction of perfluoroallylfluorosulfate derivatives of formula:

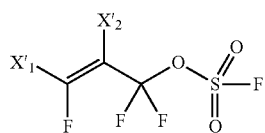

with a bis-hypofluorite of formula:

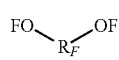

so as to obtain corresponding adduct of formula:

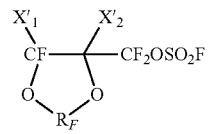

which yields by hydrolysis the target compound (IV).

Hydrolysis of above mentioned adduct is preferably accomplished by alkaline hydrolysis with an aqueous inorganic base, e.g. with aqueous KOH, optionally followed by treatment with an aqueous acidic solution (e.g. $HCl_{aq}$) for obtaining carboxylic acids and/or further neutralisation for introducing required counter-cation onto the carboxylic group.

In an alternative method for preparing cyclic fluorocompounds of formula (IV) here above, a cyclic fluoroolefin is reacted with carbonyl fluoride in the presence of fluorides, as sketched in scheme herein below:

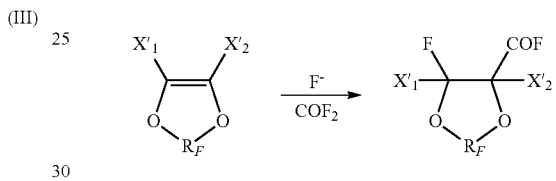

wherein $X'_1$, $X'_2$, $R_F$ have the meaning as above defined.

So obtained carbonyl fluoride derivative can be easily hydrolized to yield the target compound (IV).

In a further alternative method, cyclic fluorocompound of formula (IV) can be prepared by adding to a cyclic fluoroolefin methanol for obtaining a cyclic fluorinated methanol derivative, as sketched in the scheme herein below:

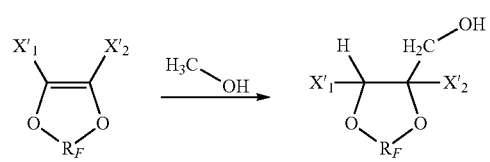

wherein $X'_1$, $X'_2$ and $R_F$ have the meaning as above defined. Cyclic alcohol derivative can be further transformed in compound (IV) via following steps:

(i) esterification of the cyclic alcohol with a fluorinated acyl fluoride yielding the corresponding ester:

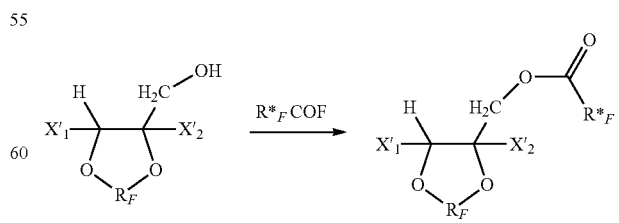

(ii) complete fluorination of all C—H bonds in C—F bonds of this latter to yield corresponding perfluorinated ester compound:

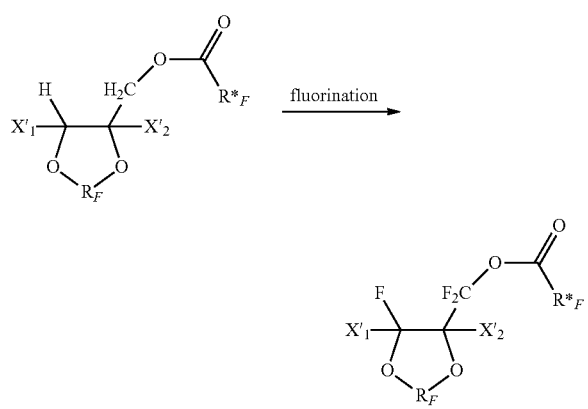

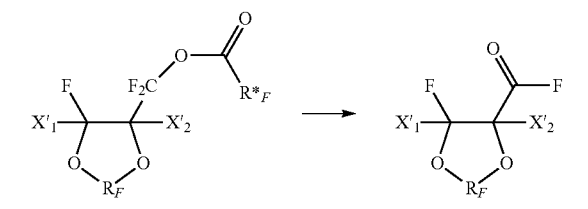

(iii) decomposition of the perfluoroester to yield the corresponding perfluoroacyl compound:

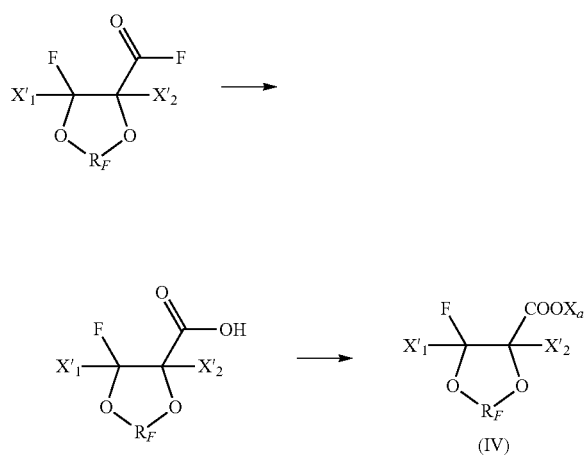

(iv) hydrolysis and treatment with a base for yielding the corresponding carboxylate derivative (IV):

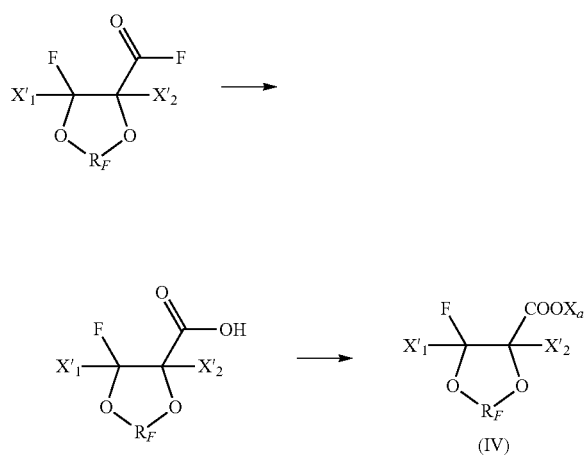

wherein in all formulae herein above $X'_1$, $X'_2$, $R_F$ and $X_a$ have the meaning as above defined; $R*_F$ is a (per)fluorocarbon group.

Any other process enabling complete fluorination of the C—H bonds, but preserving alcohol/carboxylic functionality under protected form can be also suitable for transforming above mentioned cyclic fluorinated methanol derivative in compound (IV).

The cyclic fluorocompound (IV) of the first variant of this preferred embodiment more preferably complies with formula (V):

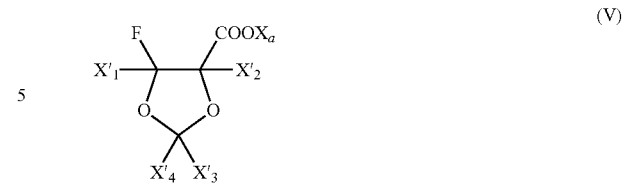

wherein $X'_1$, $X'_2$, $X'_3$, $X'_4$, equal to or different from each other are independently a fluorine atom, —$R'_f$ or —$OR'_f$, wherein $R'_f$ is a $C_{1-3}$ perfluoroalkyl group.

Non limitative examples of cyclic fluorocompounds of formula (V) are notably:

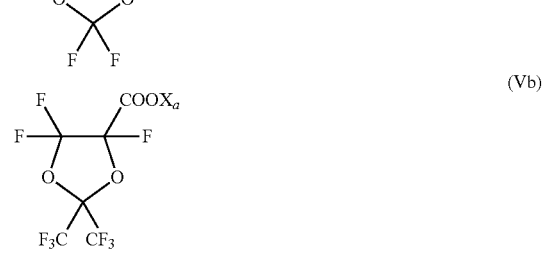

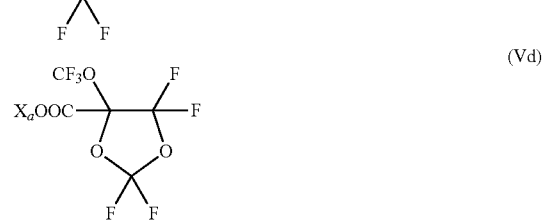

According to a second variant of this preferred embodiment, the cyclic fluorocompound complies with formula (VI) here below:

wherein $X''_1$ and $X''_2$, equal to or different from each other, are independently a fluorine atom, a —$R'_f$ group or —$OR'_f$ group, wherein $R'_f$ is a $C_{1-3}$ perfluoroalkyl group, and $R_F$ and $X_a$ have the same meanings as above defined.

Cyclic fluorocompound of formula (VI) can be prepared by adding to a cyclic fluoroolefin a hydrocarbon primary alcohol for obtaining a cyclic fluorinated alcohol derivative, as sketched in the scheme herein below:

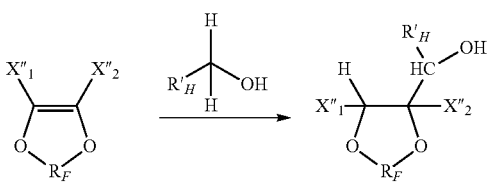
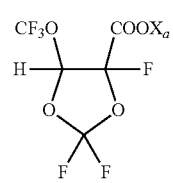

wherein $X''_1$, $X''_2$ and $R_F$ have the meaning as above defined and $R'_H$ is H or a $C_{1-6}$ hydrocarbon group.

Suitable hydrocarbon alcohols include aliphatic alcohols such as lower primary alkanols having 1 to 4 carbon atoms. Specific examples include methanol, ethanol, propanol and butanol, methanol being particularly preferred.

The reaction of the fluorinated olefin with the alcohol may be carried out as described in CHAMBERS, R. D. Fluorine in Organic Chemistry. Oxford (UK): Blackwell Publishing, 2004. ISBN 0849317908. p. 199 and ss.

The resulting cyclic fluorinated alcohol derivative can be chemically oxidized with an oxidizing agent to the corresponding carboxylic acid derivative (optionally followed by suitable hydrolysis/neutralisation steps), as depicted here below:

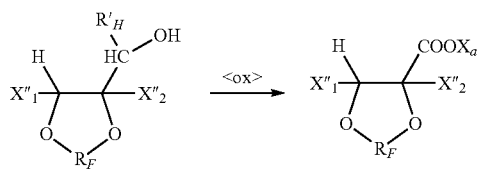

wherein $X''_1$, $X''_2$, $R'_H$, $R_F$ and $X_a$ have the same meanings as above defined.

Examples of oxidizing agents include for example potassium permanganate, chromium (VI) oxide, $RuO_4$ or $O_SO_4$ optionally in the presence of NaOCl, nitric acid/iron catalyst, dinitrogen tetroxide. Typically the oxidation is carried out in acidic or basic conditions, preferably basic conditions, at a temperature between 10° and 100° C. In addition to chemical oxidation, electrochemical oxidation may be used as well.

The cyclic fluorocompound (VI) of the second variant of this preferred embodiment more preferably complies with formula (VII):

(VII)

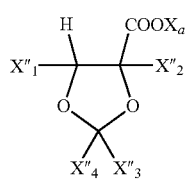

wherein $X''_1$, $X''_2$, $X''_3$, $X''_4$, equal to or different from each other are independently a fluorine atom, —$R'_f$ or —$OR'_f$, wherein $R'_f$ is a $C_{1-3}$ perfluoroalkyl group.

Non limitative examples of cyclic fluorocompounds of formula (VII) are notably:

(VIIa)
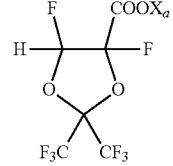

(VIIb)
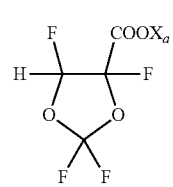

(VIIc)
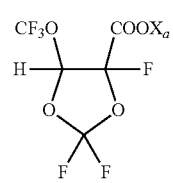

According to a second embodiment of the invention, the cyclic fluorocompound complies with formula (VIII) here below:

(VIII)
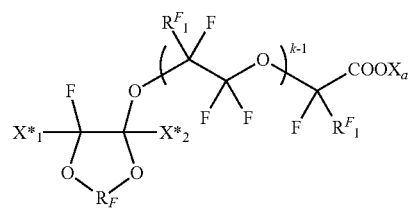

wherein $R^F$ and $X_a$ have the same meanings as above detailed; $X^*_1$, $X^*_2$ equal to or different from each other are independently a fluorine atom, —$R'_f$ or —$OR'_f$, wherein $R'_f$ is a $C_{1-3}$ perfluoroalkyl group; $R^F_1$ is F or $CF_3$, $k$ is an integer from 1 to 3.

Compounds of formula (VIII) can be notably manufactured by reaction of an unsaturated fluorodioxole with a hydrogenated glycol derivative, as sketched herein below, so as to obtain a mono-addition compound of formula (X):

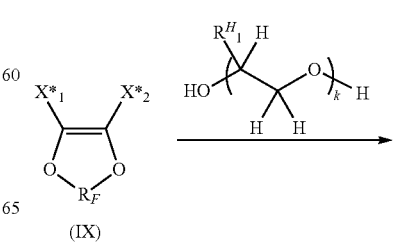

(IX)

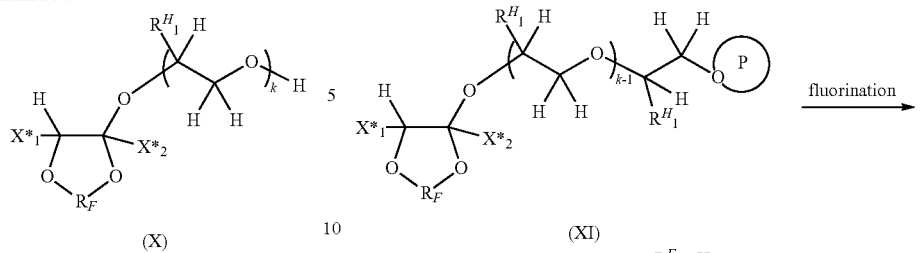

(X)

wherein X*$_1$, X*$_2$, R$_F$, k have the same meaning as above defined; R$^H_1$ is H or –CH$_3$.

Basic catalysis is generally adopted for favouring this reaction. Addition of the hydrogenated glycol derivative is generally carried out using 1 eq of said unsaturated dioxole (IX) per equivalent of base in said glycol, so as to maximize yield towards target mono-addition compound (X). As the hydroxyl functionality is generally unstable under fluorination conditions, the free hydroxyl group of the addition product (X) is generally protected before full fluorination:

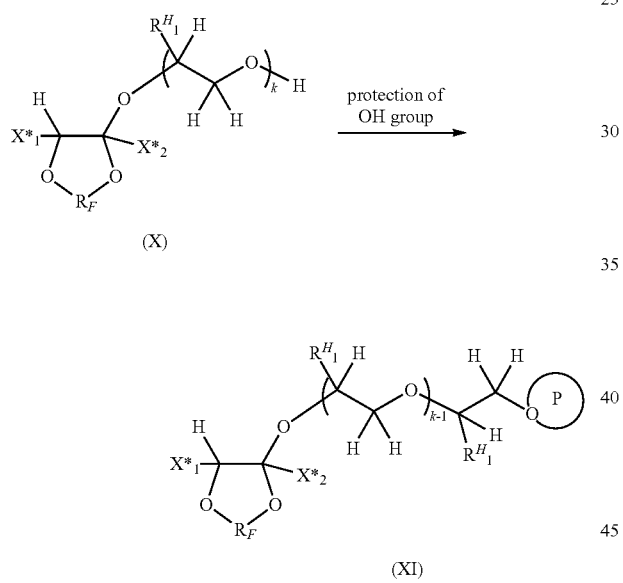

(X)

protection of OH group →

(XI)

wherein X*$_1$, X*$_2$, R$_F$, R$^H_1$, k have the meaning above defined; and round circle P denotes a protecting group.

The choice of the protecting agent is not particularly limited, provided that this group is stable under fluorination conditions. Generally, an esterification with a (per)fluorinated acyl fluoride will be the preferred route. As an alternative, reaction with any of carbonyl difluoride, carbonyl fluoride bromide and carbonyl fluoride chloride (preferably with carbonyl difluoride) can be performed on compound (X) so as to protect hydroxyl group as fluoroformate group, which is advantageously stable during fluorination.

The protected addition product (XI) (e.g. under the form of an ester or a fluoroformate) is then fluorinated according to standard procedures, typically using elemental fluorine, to yield corresponding perfluorocompound (XII):

(XI) fluorination →

(XII)

wherein X*$_1$, X*$_2$, R$_F$, R$^H_1$, R$^F_1$, k and round circle P have same meaning as above detailed.

Said perfluorocompound derivative (XII) is then submitted to appropriate reaction conditions for decomposing/hydrolyzing protecting group of the hydroxyl function, so as to yield corresponding acyl fluoride which is then converted by hydrolysis/neutralization in target compound (VIII):

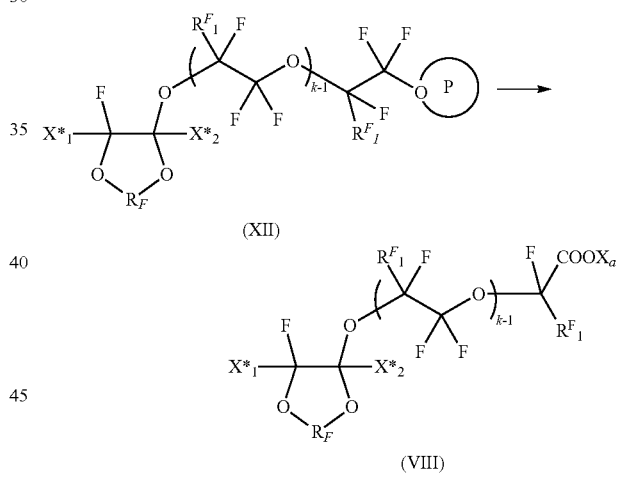

(XII) →

(VIII)

wherein X*$_1$, X*$_2$, R$_F$, R$^F_1$, X$_a$, k and round circle P have same meaning as above detailed.

This synthetic pathway can be notably applied with success for converting unsaturated perfluorodioxoles of formulae:

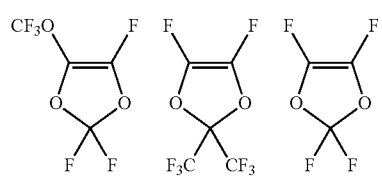

in corresponding cyclic fluorocompounds (VIII) by reaction with ethylene glycol, reaction with a fluoroacyl compound (e.g. (CF$_3$)$_2$—CF—COF) to yield corresponding ester or reaction with a carbonyl fluoride (e.g. $COF_2$) to yield corresponding fluoroformate, fluorination to yield corresponding perfluoroester or perfluoroformate, decomposition of said perfluoroester or perfluoroformate and final hydrolysis/neutralization, as sketched in following scheme:

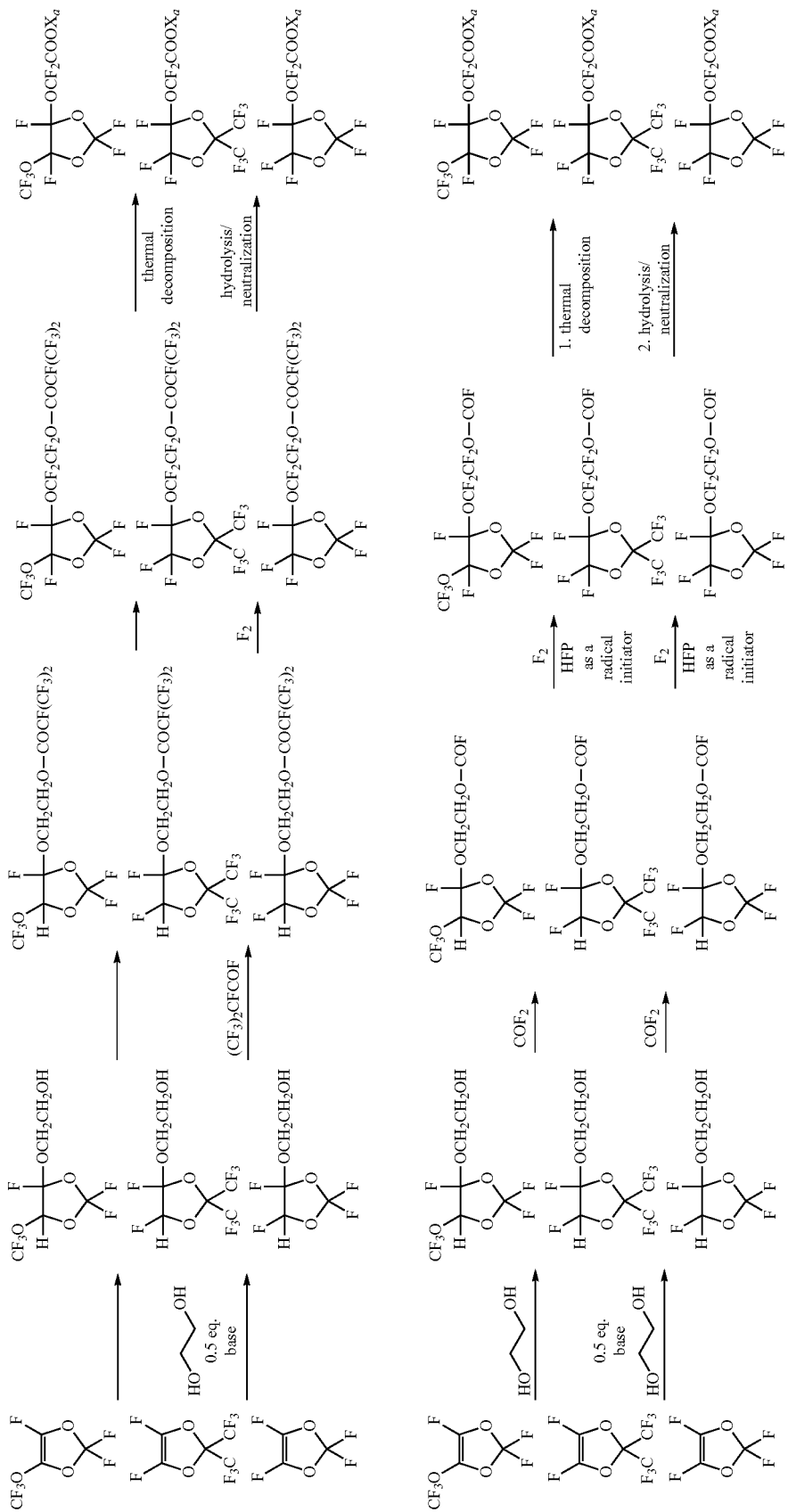

wherein $X_a$ has the same meaning as above defined. It is also understood that other acyl fluorides than $(CF_3)_2CFCOF$ or other carbonyl fluorides other than $COF_2$ can be used for protecting hydroxyl moiety, such as e.g. $CF_3COF$.

Perfluoroester and/or perfluoroformate can be notably broken to yield the corresponding acyl fluoride by thermal decomposition in the presence of a nucleophile or an electrophyle, typically in the presence of a metal fluoride of formula $MeF_y$, with Me being a metal having y valence, y being 1 or 2, in particular in the presence of NaF, $CaF_2$, AgF, CsF, KF, preferably KF.

Otherwise, perfluoroester and/or perfluoroformate can be hydrolyzed in aqueous medium, generally in the presence of suitable HF absorber, e.g. KF, which is known to capture HF yielding $KHF_2$ in aqueous medium.

Among these compounds, cyclic fluorocompound of formula (XIII), sketched here below:

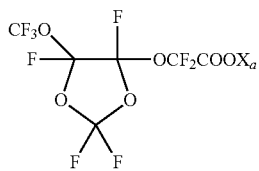

(XIII)

wherein $X_a$ has the meaning above defined, has been found particularly useful in the process of the invention.

More generally, synthetic approach detailed herein above for second embodiment of the invention, can be successfully applied for yielding cyclic fluorocompounds complying with formula (XIV) here below, which constitute a further embodiment of the invention:

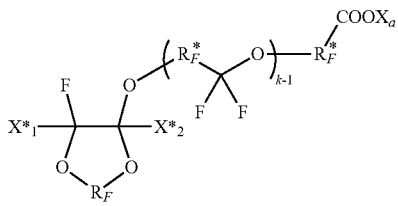

(XIV)

wherein $R_F$ and $X_a$ have the same meanings as above detailed; $X^*_1$, $X^*_2$ equal to or different from each other are independently a fluorine atom, —$R'_f$ or —$OR'_f$, wherein $R'_f$ is a $C_{1-3}$ perfluoroalkyl group; $R^*_F$ is a divalent fluorinated group, k is an integer from 1 to 3.

Compounds of formula (XIV) can be manufactured following similar pathway as above detailed for compounds of formula (VIII) by reaction of an unsaturated fluorodioxole with a hydrogenated diol derivative, provided that such diol comprises at least one —$CH_2OH$ moiety, as sketched herein below, so as to obtain a mono-addition compound of formula (VX):

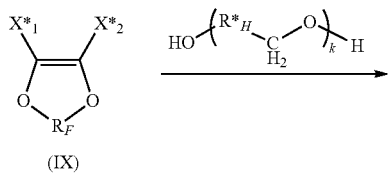

(IX)

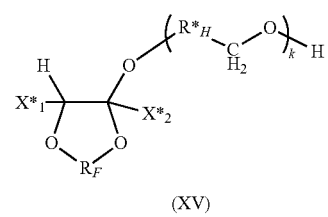

(XV)

wherein $X^*_1$, $X^*_2$, $R_F$, k have the same meaning as above defined; $R^*_H$ is a divalent hydrogenated group.

Protection of hydroxyl functionality and fluorination, followed by decomposing/hydrolyzing protecting group of the hydroxyl function, so as to yield corresponding acyl fluoride, and final hydrolysis/neutralization in target compound (XIV) can be carried out as above detailed for compounds (VIII):

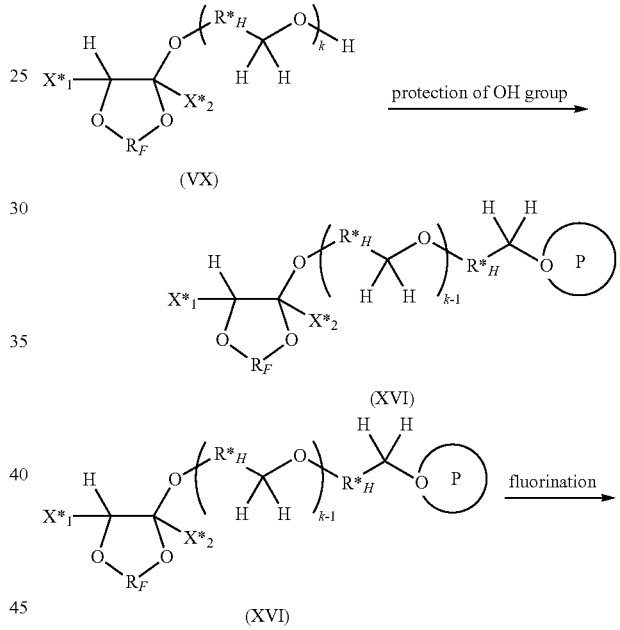

(VX)

protection of OH group (XVI)

fluorination (XVI)

(XVII)

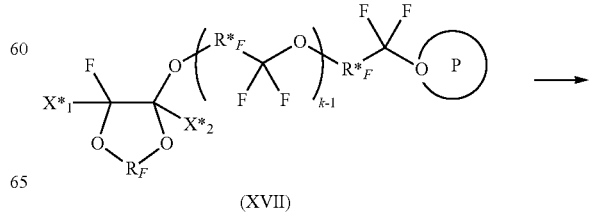

(XVII)

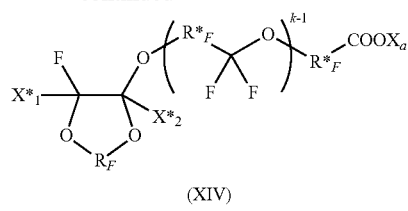

(XIV)

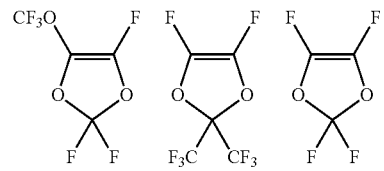

wherein $X^*_1$, $X^*_2$, $R_F$, $R^*_F$, $R^*_H$, k have the meaning above defined; and round circle P denotes a protecting group.

The choice of the protecting agent is not particularly limited, provided that this group is stable under fluorination conditions. Generally, an esterification with a (per)fluorinated acyl fluoride or formation of fluoroformate with a carbonyl fluoride will be the preferred routes.

This synthetic pathway can be notably applied with success for converting unsaturated perfluorodioxole of formulae:

in corresponding cyclic fluorocompounds (XIV) by reaction with different diols, like, notably propylene glycol, reaction with a fluoroacyl compound (e.g. $CF_3$—COF) to yield corresponding ester or reaction with a carbonyl fluoride (e.g. $COF_2$) to yield corresponding fluoroformate, fluorination to yield corresponding perfluoroester, decomposition of said perfluoroester or perfluoroformate and final hydrolysis/neutralization, as sketched in following scheme:

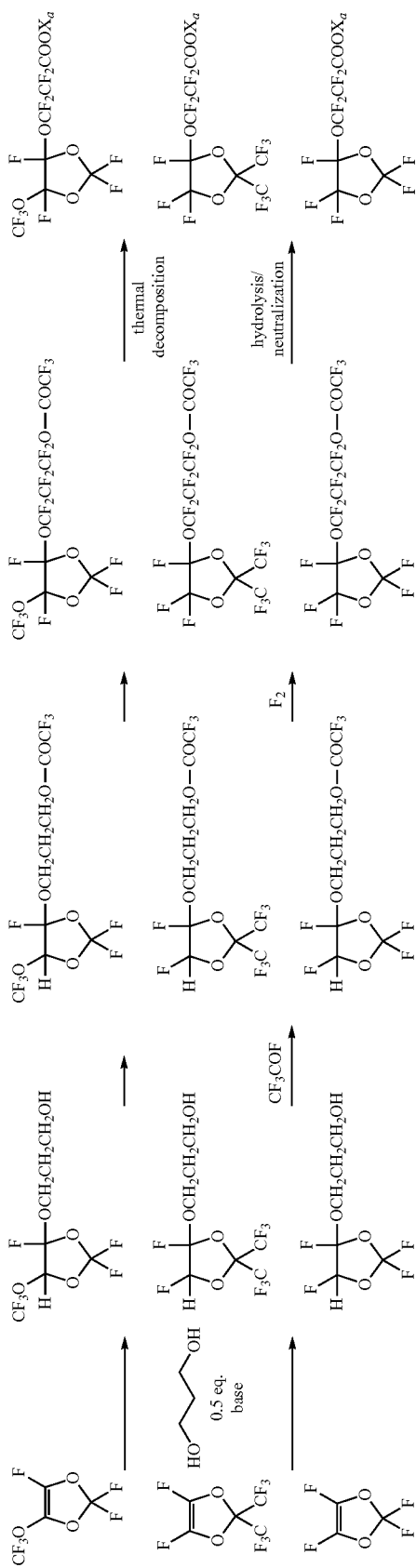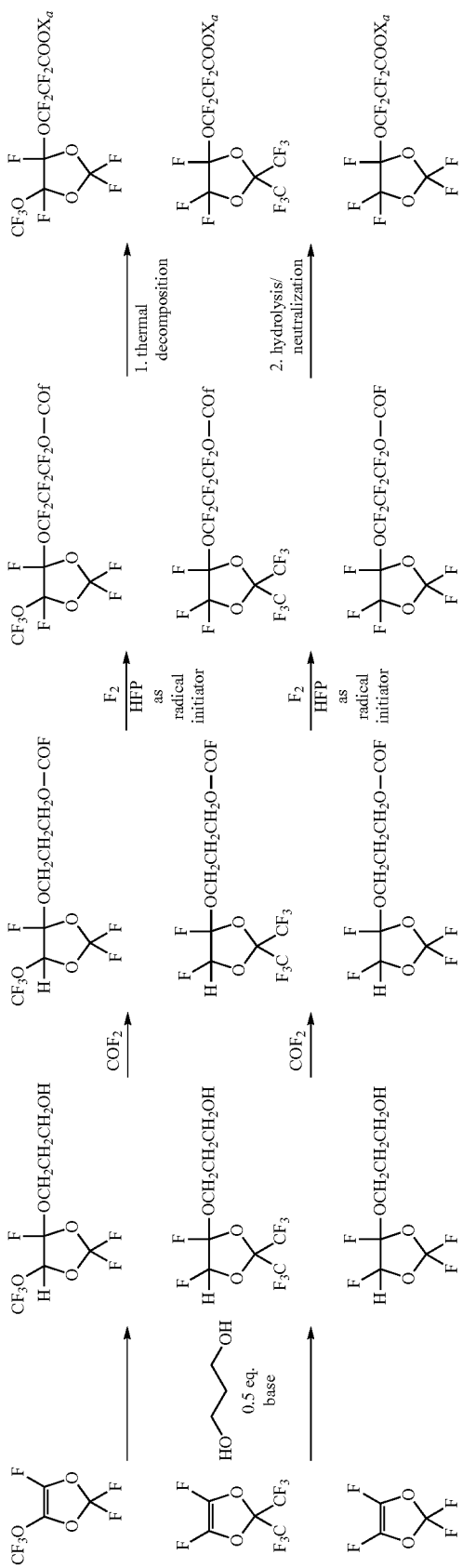

Among these compounds, cyclic fluorocompound of formula (XVIII), sketched here below:

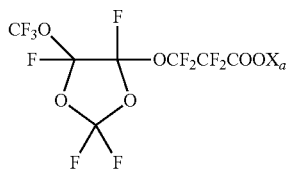

(XVIII)

wherein $X_a$ has the meaning above defined, has been found particularly useful in the process of the invention.

In the process of the invention, one or more cyclic fluorocompound of formula (I) are used in the aqueous emulsion polymerization of one or more fluorinated monomers, in particular gaseous fluorinated monomers.

By gaseous fluorinated monomers is meant monomers that are present as a gas under the polymerization conditions. In a particular embodiment, the polymerization of the fluorinated monomers is started in the presence of the cyclic fluorocompound of formula (I), i.e. the polymerization is initiated in the presence of the same. The amount of cyclic fluorocompound of formula (I) used may vary depending on desired properties such as amount of solids, particle size etc. . . . Generally the amount of cyclic fluorocompound of formula (I) will be between 0.001% by weight based on the weight of water in the polymerization and 5% by weight. A practical range is between 0.05% by weight and 1% by weight.

While the polymerization is generally initiated in the presence of the cyclic fluorocompound of formula (I), it is not excluded to add further cyclic fluorocompound of formula (I) during the polymerization, although such will generally not be necessary.

Nevertheless, it may be desirable to add certain monomer to the polymerization in the form of an aqueous emulsion. For example, fluorinated monomers and in particular perfluorinated co-monomers that are liquid under the polymerization conditions may be advantageously added in the form of an aqueous emulsion. Such emulsion of such co-monomers is preferably prepared using cyclic fluorocompound of formula (I) as an emulsifier.

The aqueous emulsion polymerization may be carried out at a temperature between 10 to 150° C., preferably 20° C. to 130° C. and the pressure is typically between 2 and 50 bar, in particular 5 to 35 bar.

The reaction temperature may be varied during the polymerization e.g. for influencing the molecular weight distribution, i.e., to obtain a broad molecular weight distribution or to obtain a bimodal or multimodal molecular weight distribution.

The pH of the polymerization media may be in the range of pH 2-11, preferably 3-10, most preferably 4-10.

The aqueous emulsion polymerization is typically initiated by an initiator including any of the initiators known for initiating a free radical polymerization of fluorinated monomers. Suitable initiators include peroxides and azo compounds and redox based initiators. Specific examples of peroxide initiators include, hydrogen peroxide, sodium or barium peroxide, diacylperoxides such as diacetylperoxide, disuccinyl peroxide, dipropionylperoxide, dibutyrylperoxide, dibenzoylperoxide, di-ter-butyl-peroxide, benzoylacetylperoxide, diglutaric acid peroxide and dilaurylperoxide, and further per-acids and salts thereof such as e.g. ammonium, sodium or potassium salts. Examples of peracids include peracetic acid. Esters of the peracid can be used as well and examples thereof include tert.-butylperoxyacetate and tert.-butylperoxypivalate. Examples of inorganic initiators include for example ammonium-alkali- or earth alkali salts of persulfates, permanganic or manganic acid or manganic acids. A persulfate initiator, e.g. ammonium persulfate (APS), can be used on its own or may be used in combination with a reducing agent. Suitable reducing agents include bisulfites such as for example ammonium bisulfite or sodium metabisulfite, thiosulfates such as for example ammonium, potassium or sodium thiosulfate, hydrazines, azodicarboxylates and azodicarboxyldiamide (ADA). Further reducing agents that may be used include sodium formaldehyde sulfoxylate (Rongalite) or fluoroalkyl sulfinates as disclosed in U.S. Pat. No. 5,285,002. The reducing agent typically reduces the half-life time of the persulfate initiator. Additionally, a metal salt catalyst such as for example copper, iron or silver salts may be added. The amount of initiator may be between 0.01% by weight (based on the fluoropolymer solids to be produced) and 1% by weight. In one embodiment, the amount of initiator is between 0.05 and 0.5% by weight. In another embodiment, the amount may be between 0.05 and 0.3% by weight.

The aqueous emulsion polymerization can be carried out in the presence of other materials, such as notably buffers and, if desired, complex-formers or chain-transfer agents.

Examples of chain transfer agents that can be used include dimethyl ether, methyl t-butyl ether, alkanes having 1 to 5 carbon atoms such as ethane, propane and n-pentane, halogenated hydrocarbons such as $CCl_4$, $CHCl_3$ and $CH_2Cl_2$ and hydrofluorocarbon compounds such as $CH_2F$—$CF_3$ (R134a). Additionally esters like ethylacetate, malonic esters can be effective as chain transfer agent in the process of the invention.

Examples of fluorinated monomers that may be polymerized using the cyclic fluorocompound according to formula (I) as an emulsifier in the process of the invention include partially or fully fluorinated gaseous monomers including fluorinated olefins such as tetrafluoroethylene (TFE), chlorotrifluoroethylene (CTFE), hexafluoropropylene (HFP), vinyl fluoride (VF), vinylidene fluoride (VDF), partially or fully fluorinated allyl ethers and partially or fully fluorinated alkyl or alkoxy-vinyl ethers.

Further, the aqueous emulsion polymerization can be carried out in the presence of fluorinated fluids, typically enabling formation of nanosized droplets (average size of less than 50 nm, preferably of less than 30 nm) stabilized in aqueous dispersion by the presence of the cyclic fluorocompound of formula (I).

Should the process of the invention be carried out in the presence of a fluorinated fluid, as above detailed, it may be preferable to first homogenously mix cyclic compound and said fluid in aqueous phase, possibly in an aqueous medium, and then feeding an aqueous mixture of compound (I) and said fluid in the polymerization medium. This technique is particularly advantageous as this pre-mix can advantageously enable manufacture of an emulsion of said fluid in an aqueous phase comprising the cyclic compound, wherein this emulsion comprises dispersed droplets of said fluid having an average size of preferably less than 50 nm, more preferably of less than 40 nm, even more preferably of less than 30 nm.

Fluids which can be used according to this embodiment are preferably (per)fluoropolyethers comprising recurring units (R1), said recurring units comprising at least one ether linkage in the main chain and at least one fluorine atom (fluoropolyoxyalkene chain). Preferably the recurring units R1 of the (per)fluoropolyether are selected from the group consisting of:
(I) —CFX—O—, wherein X is —F or —CF$_3$; and
(II) —CF$_2$—CFX—O—, wherein X is —F or —CF$_3$; and
(III) —CF$_2$—CF$_2$—CF$_2$—O—; and
(IV) —CF$_2$—CF$_2$—CF$_2$—CF$_2$—O—; and
(V) —(CF$_2$)$_j$—CFZ—O— wherein j is an integer chosen from 0 and 1 and Z is a fluoropolyoxyalkene chain comprising from 1 to 10 recurring units chosen among the classes (I) to (IV) here above; and mixtures thereof.

Should the (per)fluoropolyether comprise recurring units R1 of different types, advantageously said recurring units are randomly distributed along the fluoropolyoxyalkene chain.

Preferably the (per)fluoropolyether is a compound complying with formula (I-p) here below:

$$T_1\text{-}(CFX)_p\text{—}O\text{—}R_f\text{—}(CFX)_{p'}\text{-}T_2 \qquad (I\text{-}p)$$

wherein:
each of X is independently F or CF$_3$;
p and p', equal to or different from each other, are integers from 0 to 3;
R$_f$ is a fluoropolyoxyalkene chain comprising repeating units R°, said repeating units being chosen among the group consisting of:
(i) —CFXO—, wherein X is F or CF$_3$,
(ii) —CF$_2$CFXO—, wherein X is F or CF$_3$,
(iii) —CF$_2$CF$_2$CF$_2$O—,
(iv) —CF$_2$CF$_2$CF$_2$CF$_2$O—,
(v) —(CF$_2$)$_j$—CFZ—O— wherein j is an integer chosen from 0 and 1 and Z is a group of general formula —OR$_f'$T$_3$, wherein R$_f'$ is a fluoropolyoxyalkene chain comprising a number of repeating units from 0 to 10, said recurring units being chosen among the followings: —CFXO—, —CF$_2$CFXO—, —CF$_2$CF$_2$CF$_2$O—, —CF$_2$CF$_2$CF$_2$CF$_2$O—, with each of each of X being independently F or CF$_3$; and T$_3$ is a C$_1$-C$_3$ perfluoroalkyl group, and mixtures thereof;
T$_1$ and T$_2$, the same or different from each other, are H, halogen atoms, C$_1$-C$_3$ fluoroalkyl groups, optionally comprising one or more H or halogen atoms different from fluorine.

The polymerization may further involve non-fluorinated monomers such as ethylene and propylene.

Further examples of fluorinated monomer that may be used in the aqueous emulsion polymerization according to the invention include those corresponding to the formula: CF$_2$=CF—O—R$_f$ wherein R$_f$ represents a perfluorinated aliphatic group that may contain one or more oxygen atoms.

Still further, the polymerization may involve comonomers that have a functional group such as for example a group capable of participating in a peroxide cure reaction. Such functional groups include halogens such as Br or I as well as nitrile groups.

The aqueous emulsion polymerization may be used to produce a variety of fluoropolymers including perfluoropolymers, which have a fully fluorinated backbone, as well as partially fluorinated fluoropolymers. Also the aqueous emulsion polymerization may result in melt-processable fluoropolymers as well as those that are not melt-processable such as for example polytetrafluoroethylene and so-called modified polytetrafluoroethylene. The polymerization process can further yield fluoropolymers that can be cured to make fluoroelastomers as well as fluorothermoplasts.

Fluorothermoplasts are generally fluoropolymers that have a distinct and well noticeable melting point, typically in the range of 60 to 320° C. or between 100 and 320° C. They thus have a substantial crystalline phase. Fluoropolymers that are used for making fluoroelastomers typically are amorphous and/or have a negligible amount of crystallinity such that no or hardly any melting point is discernable for these fluoropolymers.

According to an embodiment of the method of the invention, the method comprises polymerizing in aqueous emulsion in the presence of a mixture of the cyclic fluorocompound of formula (I) and at least one further emulsifier different from cyclic fluorocompound of formula (I).

The choice of said additional emulsifier is not particularly limited. Generally fluorinated emulsifiers will be used in combination with cyclic fluorocompound of formula (I).

More specifically, fluorinated emulsifier [surfactant (FS)] of formula:

$$R_{fS}(X^-)_j(M^+)_j$$

wherein R$_{fS}$ is a C$_3$-C$_{30}$ (per)fluoroalkyl chain, (per)fluoro (poly)oxyalkylenic chain, X$^-$ is —COO$^-$, —PO$_3^-$ or —SO$_3^-$, M$^+$ is selected from H$^+$, NH$_4^+$, an alkaline metal ion and j can be 1 or 2.

As non limitative example of surfactants (FS), mention may be made of ammonium and/or sodium perfluorocarboxylates, and/or (per)fluoropolyoxyalkylenes having one or more carboxylic end groups.

Other examples of fluorinated surfactants are (per)fluorooxyalkylenic surfactants described in US 2007015864 (3M INNOVATIVE PROPERTIES) 8, Jan. 2007, US 2007015865 (3M INNOVATIVE PROPERTIES CO) 18, Jan. 2007, US 2007015866 (3M INNOVATIVE PROPERTIES CO) 18, Jan. 2007, US 2007025902 (3M INNOVATIVE PROPERTIES CO) 1, Feb. 2007.

More preferably, the fluorinated emulsifier [surfactant (FS)] is chosen from:
CF$_3$(CF$_2$)$_{n1}$COOM', in which n$_1$ is an integer ranging from 4 to 10, preferably from 5 to 7, and more preferably being equal to 6; M' represents H, NH$_4$, Na, Li or K, preferably NH$_4$;
T(C$_3$F$_6$O)$_{n0}$(CFXO)$_{m0}$CF$_2$COOM'', in which T represents Cl or a perfluoroalkoxyde group of formula C$_k$F$_{2k+1}$O with k is an integer from 1 to 3, one F atom being optionally substituted by a Cl atom; n$_0$ is an integer ranging from 1 to 6; m$_0$ is an integer ranging from 0 to 6; M'' represents H, NH$_4$, Na, Li or K; X represents F or CF$_3$;
F—(CF$_2$—CF$_2$)$_{n2}$—CH$_2$—CH$_2$—RO$_3$M''', in which R is P or S, preferably S, M''' represents H, NH$_4$, Na, Li or K, preferably H; n$_2$ is an integer ranging from 2 to 5, preferably n$_2$=3;
A-R$_f$-B bifunctional fluorinated surfactants, in which A and B, equal to or different from each other, are —(O)$_p$CFX—COOM*; M* represents H, NH$_4$, Na, Li or K, preferably M* represents NH$_4$; X=F or CF$_3$; p is an integer equal to 0 or 1; R$_f$ is a linear or branched perfluoroalkyl chain, or a (per)fluoropolyether chain such that the number average molecular weight of A-R$_f$-B is in the range 300 to 3,000, preferably from 500 to 2,000;
R'$_f$—O—(CF$_2$)$_r$—O-L-COOM', wherein R'$_f$ is a linear or branched perfluoroalkyl chain, optionally comprising catenary oxygen atoms, M' is H, NH$_4$, Na, Li or K, preferably M' represents NH$_4$; r is 1 to 3; L is a bivalent fluorinated bridging group, preferably —CF$_2$CF$_2$— or —CFX—, X=F or CF$_3$;
—R''$_f$—(OCF$_2$)$_u$—O—(CF$_2$)$_v$—COOM'', wherein R''$_f$ is a linear or branched perfluoroalkyl chain, optionally comprising catenary oxygen atoms, M" is H, $NH_4$, Na, Li or K, preferably M" represents $NH_4$; u and v are integers from 1 to 3;

R'''$_f$—(O)$_t$—CHQ-L-COOM''', wherein R'''$_f$ is a linear or branched perfluoroalkyl chain, optionally comprising catenary oxygen atoms, Q=F or $CF_3$, t is 0 or 1, M''' is H, $NH_4$, Na, Li or K, preferably M''' is $NH_4$; L is a bivalent fluorinated bridging group, preferably —$CF_2CF_2$— or —CFX—, X=F or $CF_3$;

and mixtures thereof.

Particular good results have been obtained with mixtures of compound (I) with A-R$_f$-B bifunctional fluorinated surfactants; said bifunctional surfactant A-R$_f$-B preferably complies with formula $M_z$OOC—CFX$_z$—O—R$_{fz}$—CFX$_z$—COOM$_z$, wherein $M_z$ is H, $NH_4$, Na, Li or K, preferably $M_z$ is $NH_4$; $X_z$=F, —$CF_3$; $R_{fz}$ is a (per)fluoropolyether chain comprising recurring units complying with one or more of formulae: —($C_3F_6O$)—; —($CF_2CF_2O$)—; —($CFL_OO$)—, wherein $L_O$=F, —$CF_3$, —($CF_2(CF_2)_{z'}CF_2O$)—, wherein z' is 1 or 2; —($CH_2CF_2CF_2O$)—.

$R_{fz}$ preferably has one of the following structures:

1) —($CF_2O$)$_a$—($CF_2CF_2O$)$_b$— wherein a and b≥0; should a and b be simultaneously >0, b/a ratio is generally comprised between 0.01 and 10, extremes included;

2) —($CF_2$—($CF_2$)$_{z'}$—$CF_2O$)$_{b'}$—, with b'>0 and z' being 1 or 2;

3) —($C_3F_6O$)$_r$—($C_2F_4O$)$_b$—($CFL_OO$)$_t$—, wherein r, b and t≥0, $L_O$=F, —$CF_3$; should r, b and t be simultaneously >0, r/b ratio is typically comprised in the range 0.5-2.0 and (r+b)/t in the range 10-30;

4) —($OC_3F_6$)$_r$—($OCFL_O$)$_t$—$OCF_2$—R*$_f$—$CF_2O$—($C_3F_6O$)$_r$—($CFL_OO$)$_t$—, wherein R*$_f$ is a fluoroalkylene group from 1 to 4 carbon atoms; $L_O$=F, —$CF_3$; r, t being ≥0.

Most preferred A-R$_f$-B bifunctional fluorinated surfactant complies with formula $M_z$OOC—CFX$_z$—O—($CF_2O$)$_a$—($CF_2CF_2O$)$_b$—CFX$_z$—COOM$_z$, wherein $M_z$ is H, $NH_4$, Na, Li or K, preferably $M_z$ is $NH_4$; $X_z$=F, —$CF_3$; and a, b, both >0, are selected so that b/a is comprised between 0.3 and 10 and the molecular weight of the surfactant is comprised between 500 and 2000.

Should the process of the invention be carried out in the presence of mixture of cyclic compound and further fluorinated emulsifier, as above detailed, it may be preferable to first homogenously mix cyclic compound and further emulsifier in aqueous phase, and then feeding an aqueous mixture of compound (I) and said emulsifier in the polymerization medium. This technique is particularly advantageous when the further fluorinated emulsifier is poorly soluble in water. Thus, this pre-mix can advantageously enable manufacture of an emulsion of said fluorinated emulsifier in an aqueous phase comprising the cyclic compound, wherein this emulsion comprises dispersed droplets of said fluorinated emulsifier having an average size of preferably less than 50 nm, preferably of less than 40 nm, more preferably of less than 30 nm.

Further, in addition, the aqueous emulsion polymerization of this embodiment can be carried out in the presence of fluorinated fluids, as above referred, typically enabling formation of nanosized droplets (average size of less than 50 nm, preferably less than 30 nm) stabilized in aqueous dispersion by the presence of the mixture of the cyclic fluorocompound of formula (I) and at least one further emulsifier different from cyclic fluorocompound of formula (I).

Fluorinated fluids which can be used in combination with said mixture of compound (I) and emulsifier are those above referred, suitable for being used in combination with the cyclic fluorocompound of formula (I).

The aqueous emulsion polymerization process of the invention results in a dispersion of the fluoropolymer in water comprising the cyclic fluorocompound of formula (I). Generally the amount of solids of the fluoropolymer in the dispersion directly resulting from the polymerization will vary between 3% by weight and about 40% by weight depending on the polymerization conditions. A typical range is between 5 and 30% by weight, for example between 10 and 25% by weight.

The particle size (volume average diameter) of the fluoropolymer is typically between 40 nm and 400 nm with a typical particle size between 60 nm and about 350 nm being preferred. The total amount of cyclic fluorocompound formula (I) in the resulting dispersion is typically between 0.001 and 5% by weight based on the amount of fluoropolymer solids in the dispersion. A typical amount may be from 0.01 to 2% by weight or from 0.02 to 1% by weight.

The fluoropolymer may be isolated from the dispersion by coagulation if a polymer in solid form is desired. Also, depending on the requirements of the application in which the fluoropolymer is to be used, the fluoropolymer may be post-fluorinated so as to convert any thermally unstable end groups into stable $CF_3$— end groups.

For coating applications, an aqueous dispersion of the fluoropolymer is desired and hence the fluoropolymer will not need to be separated or coagulated from the dispersion. To obtain a fluoropolymer dispersion suitable for use in coating applications such as for example in the impregnation of fabrics or in the coating of metal substrates to make for example cookware, it will generally be desired to add further stabilizing surfactants and/or to further increase the fluoropolymer solids. For example, non-ionic stabilizing surfactants may be added to the fluoropolymer dispersion. Typically these will be added thereto in an amount of 1 to 12% by weight based on fluoropolymer solids. Examples of non-ionic surfactants that may be added include $R^1$—O—[$CH_2CH_2O$]$_n$—[$R^2O$]$_m$—$R^3$ (NS) wherein $R^1$ represents an aromatic or aliphatic hydrocarbon group having from 6 to 18 carbon atoms, $R^2$ represents an alkylene having 3 carbon atoms, $R^3$ represents hydrogen or a Cl_3 alkyl group, n has a value of 0 to 40, m has a value of 0 to 40 and the sum of n+m being at least 2. It will be understood that in the above formula (NS), the units indexed by n and m may appear as blocks or they may be present in an alternating or random configuration. Examples of non-ionic surfactants according to formula (VI) above include alkylphenol oxy ethylates such as ethoxylated p-isooctylphenol commercially available under the brand name TRITON™ such as for example TRITON™ X 100 wherein the number of ethoxy units is about 10 or TRITON™ X 114 wherein the number of ethoxy units is about 7 to 8. Still further examples include those in which $R^1$ in the above formula (NS) represents an alkyl group of 4 to 20 carbon atoms, m is 0 and $R^3$ is hydrogen. An example thereof includes isotridecanol ethoxylated with about 8 ethoxy groups and which is commercially available as GENAPOL® X080 from Clariant GmbH. non-ionic surfactants according to formula (NS) in which the hydrophilic part comprises a block-copolymer of ethoxy groups and propoxy groups may be used as well. Such non-ionic surfactants are commercially available from Clariant GmbH under the trade designation GENAPOL® PF 40 and GENAPOL® PF 80.

The amount of fluoropolymer solids in the dispersion may be upconcentrated as needed or desired to an amount between 30 and 70% by weight. Any of the known upconcentration techniques may be used including ultrafiltration and thermal upconcentration.

Still an object of the invention are fluoropolymer dispersions comprising at least one cyclic fluorocompound of formula (I), as above described.

Said fluoropolymer dispersions are typically obtained by the process of the invention.

Concentration of cyclic fluorocompound of formula (I) in the fluoropolymer dispersions of the invention can be reduced, if necessary, following traditional techniques. Mention can be made of ultrafiltration combined with percolate recycle, as described in U.S. Pat. No. 4,369,266 (HOECHST AG) 18, Jan. 1983, treatment with ion exchange resins in the presence of a non-ionic surfactant (as described in EP 1155055 A (DYNEON GMBH) 21, Nov. 2001), of an anionic surfactant (as exemplified in EP 1676868 A (SOLVAY SOLEXIS SPA) May 7, 2006) or of a polyelectrolyte (as taught in EP 1676867 A (SOLVAY SOLEXIS SPA) May 7, 2006).

The invention thus also pertains to a process for recovering cyclic fluorocompound of formula (I) from fluoropolymer dispersions comprising the same. The process preferably comprises contacting the fluoropolymer dispersion with a solid adsorbing material, typically an ion exchange resin, preferably an anion exchange resin: the cyclic fluorocompound of formula (I) is advantageously adsorbed (at least partially) onto the solid adsorbing material. Cyclic fluorocompound of formula (I) can be efficiently recovered from solid adsorbing material by standard technique, including elution, thermal desorption and the like. In case of elution, in particular from anion exchange resin, cyclic fluorocompound of formula (I) can be recovered by elution with an acidic solution. Typically, an aqueous medium comprising an acid and a water-miscible organic solvent can be used to this aim. Mixtures of inorganic acid and alcohol in water are particularly effective. Cyclic fluorocompound (I) can be notably recovered from such liquid phases by standard methods, including, notably crystallization, distillation (e.g. under the form of ester) and the like.

Also, cyclic fluorocompound (I) as above detailed and processes for its manufacture are other objects of the present invention.

The invention will be now explained in more detail with reference to the following examples, whose purpose is merely illustrative and not intended to limit the scope of the invention.

Preparative Example 1

Synthesis of Compound VIIa (with $X_a$=$NH_4$)

Example 1a. Reaction Between perfluoro-5-methoxy-1,3-dioxole (MDO, (A) in Scheme Here Below) and Methanol

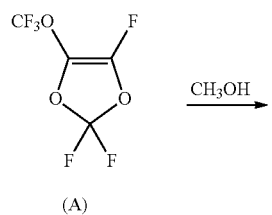

(A)

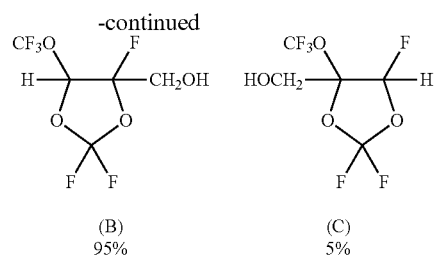

(B) 95%
(C) 5%

Figure 1:
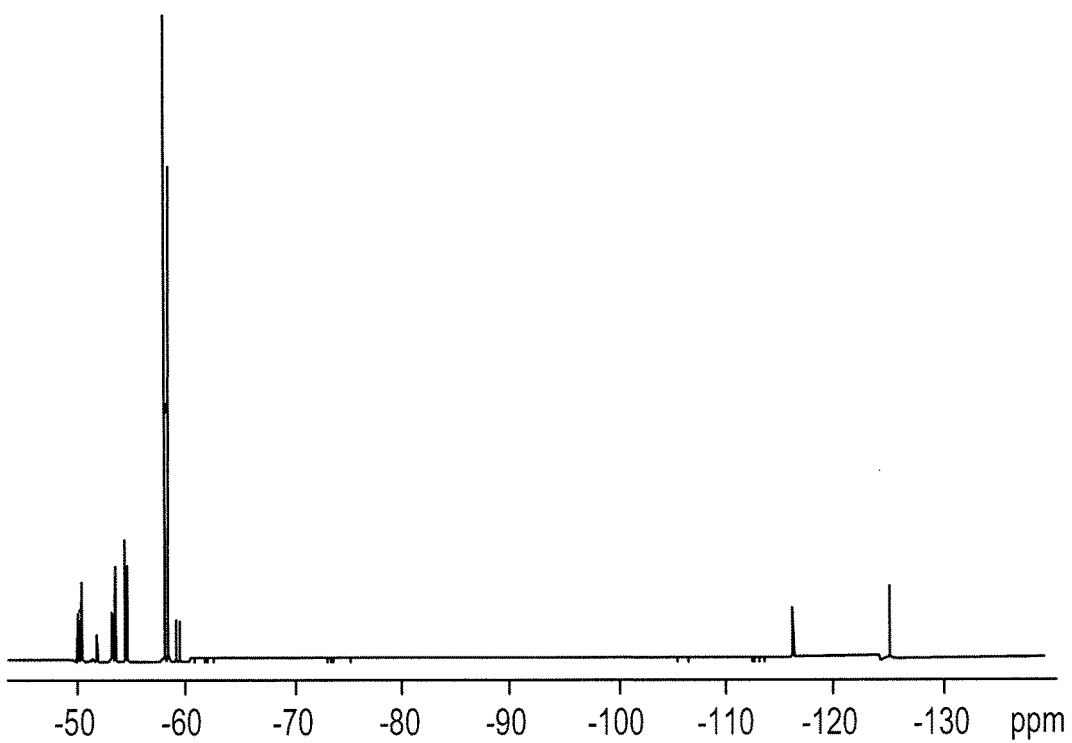
FIG. 1 depicts the $^{19}$F-NMR spectrum recorded on a compound (B)

$CaCO_3$ (7.14 mmol, 0.714 g) was introduced in a stainless steel high pressure vessel equipped with a digital manometer and a magnetic stirrer. After careful evacuation at room temperature, a mixture consisting of $CH_3OH$ (3.57 moles, 114 g), di-tert-butyl peroxide (DTBP; 71.4 mmol, 10.5 g) and MDO (0.714 mol, 150 g) was introduced into the vessel. The vessel was then heated at 134° C. under vigorous stirring for 21 hours, by monitoring internal pressure. Once the reaction completed, the vessel was cooled to room temperature and the crude reaction mixture was recovered and rinsed several times with distilled water. The organic (lower) phase is first dried over $MgSO_4$, filtered and finally distilled. Isolated yield=56% with respect to the starting MDO (A). b.p.=142° C. Selectivity=95% towards target isomer (B); 5% towards alternative isomer (C). FIG. 1 depicts the $^{19}$F-NMR spectrum recorded on compound (B).

Example 1b. Oxydation of Alcohol Intermediate (B)

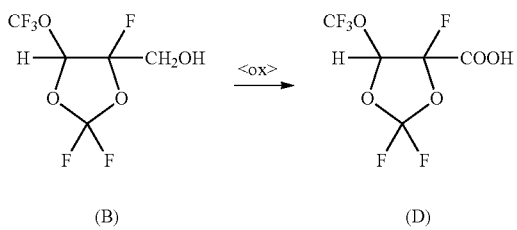

(B)                          (D)

An aqueous solution composed of $KMnO_4$ (238 mmol, 37.6 g), NaOH (238 mmol, 9.52 g) in 200 ml of distilled $H_2O$ was introduced in a 3-necked glass round-bottomed flask equipped with a magnetic stirrer, a dropping funnel, a thermometer and a tap water refrigerating column. The flask was heated to 80° C. with vigorous stirring and then 238 mmol; 50 g of product obtained from step 1a was slowly dropped into the basic oxidizing solution. Immediate exothermic release (+15° C.) was observed together with formation of $MnO_2$ precipitate. After completion of the addition, solution was further stirred at 80° C. for 40 min. Crude reaction mixture was then cooled to room temperature, filtered, acidified to pH=1 with concentrated HCl (37% w/w) and extracted several times with $CH_2Cl_2$. The organic layer was dried over $MgSO_4$, filtered and then the $CH_2Cl_2$ is evaporated. Isolated yield=55%, conversion of product from 1a=100%. $pK_a$ of (D)=2.8.

Example 1c. Synthesis of VIIa by Basic Hydrolysis of Acid (D)

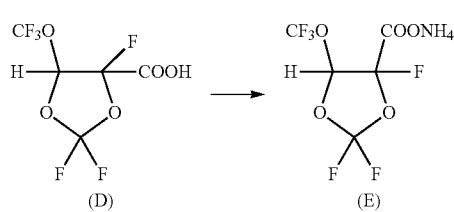

An organic solution composed of (D) (127 mmol; 30.6 g) and 200 ml of $CH_2Cl_2$ was introduced in a 2-necked glass round-bottomed flask equipped with a magnetic stirrer, a tap water refrigerating column and a bubbling tube. The mixture was cooled to 0° C. with vigorous stirring and a large excess of gaseous $NH_3$ was bubbled through the organic mixture. Bubbling of $NH_3$ (g) was pursued until completion of the precipitation of the ammonium salt. Crude mixture was filtered; solid was dried in a vacuum oven at 40° C. under reduced pressure (20 mmHg) for 2 hours. A flaky white solid is obtained. Isolated yield of compound (E) (VIIa, with $X_a$ being $NH_4$)=100%. The thermogravimetric analysis (TGA) in air points out a weight decrease of 10% at 148° C. and of 50% at 182° C. FIG. 2 depicts the $^{19}F$-NMR spectrum of compound (E). LC-MS analysis showed a strong peak at m/z=255 (corresponding to the carboxylate moiety of (E)). The oral acute toxicity of compound VIIa was evaluated according to standard practice; $LD_{50}$ was found to exceed 2000 mg/kg.

Preparative Example 2

Synthesis of Compound Va (with $X_a$=$NH_4$)

Example 2b Esterification of Alcohol Intermediate (B)

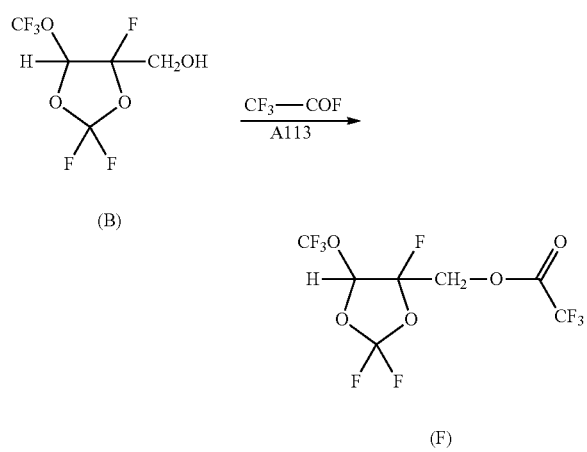

Alcohol intermediate (B) (333 mmol, 70 g) obtained from example 1a was made to react with $CF_3COF$ (350 mmol, 40, 5 g) in 200 ml of A113 at T=0° C. Solvent and unreacted $CF_3COF$ were removed by distillation at 40° C./600 mm Hg.

Example 2c Fluorination of Ester (F)

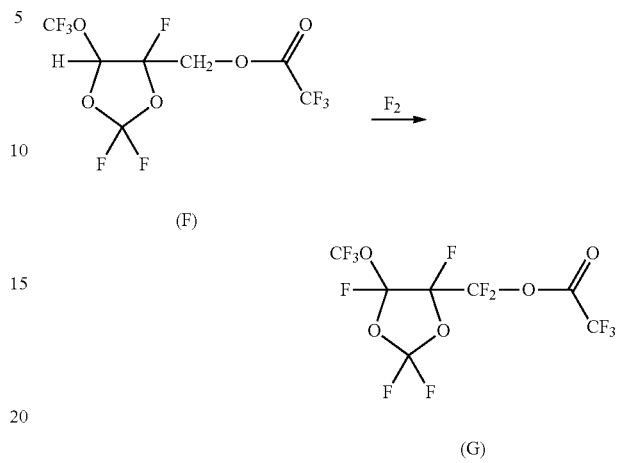

Ester (F) was diluted in A113 (200 ml) and fluorinated with a mixture $F_2/N_2$ (20/80) at a temperature of 0 to 10° C. Reaction was monitored by gas chromatography. Once fluorination completed, residual $F_2$ was vented by bubbling a flow of nitrogen. Perfluoroester (G) was recovered after removal under reduced pressure of solvent.

Example 2d Hydrolysis of Perfluorinated Ester (G)

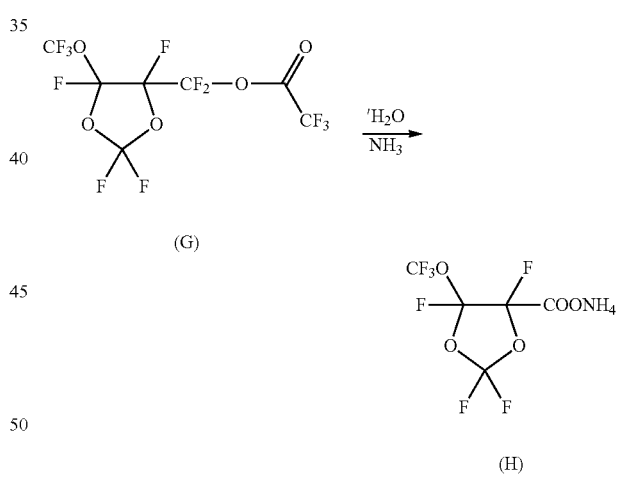

Perfluorinated ester (G) was hydrolyzed in water at 0° C., yielding corresponding acid with quantitative yield. Evolved HF was neutralized with 1.5 mol eq. of KF, yielding solid $KHF_2$, which was separated by filtration. After removal of solvent, the free acid (b.p.=160° C.) and $CF_3COOH$ (b.p.=72° C.) were separated by fractional distillation. Gaseous $NH_3$ was then bubbled in a $CH_2Cl_2$ (200 ml) solution of the acid; ammonium salt (H) (formula Va, with $X_a$=$NH_4$) was then recovered with a yield of 75% moles (with respect to alcohol intermediate (B)). The thermogravimetric analysis (TGA) in Air points out a weight decrease of 10% at 145° C. and of 50% at 182° C. FIG. 3 depicts the $^{19}F$-NMR spectrum recorded on compound (H).

Example 2e Preparation of Fluoroformate of Alcohol Intermediate (B)

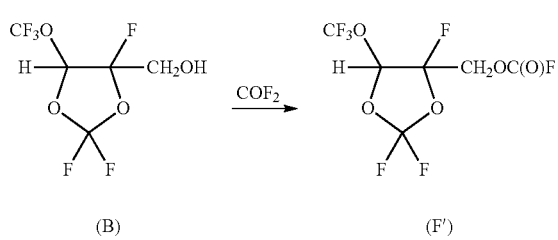

In a 250 ml stainless steel reactor equipped with mechanic stirrer, gas inlet, gas outlet, a thermocouple to check the internal temperature, and external cooling bath, 99 g of a alcohol of the above formula (B) and 34 g of powdered NaF were loaded and the external temperature set at 15° C. Then, $COF_2$ (2.0 Nl/h obtained by reaction between 2.5 Nl/h of CO and 2.0 Nl/h of $F_2$) diluted with 1.0 Nl/h of He were introduced into the reactor kept under vigorous stirring. The off-gases were analysed by a G.C. system to evaluate $COF_2$ conversion. After 6.0 hours feeding was stopped and crude mixture was filtered to separate inorganic salts. The liquid product was analyzed by $^{19}F$ NMR showing an almost quantitative conversion of the starting alcohol and selectivity in the desired fluoroformate.

Example 2f Fluorination of Fluoroformate (F')

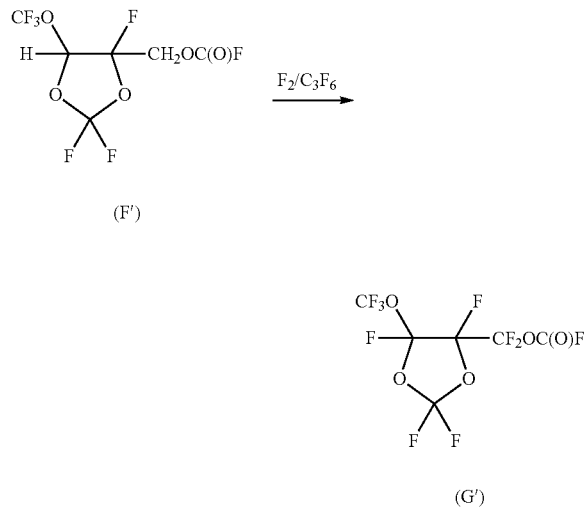

In a 250 ml stainless steel reactor equipped with mechanic stirrer, two gas inlets, one gas outlet, a thermocouple to check the internal temperature, and external cooling bath, 81 g of the fluoroformate of formula (F') were introduced and fluorinated according to the same procedure of Example 1, with the exception that $F_2$ was fed at 1.8 Nl/h, diluted with 3.0 Nl/h of He. After 15 hours, the internal temperature fell quickly from 5° C. to 0° C., and no additional $F_2$ conversion was observed. The crude mixture was collected and analyzed by GC and $^{19}F$ NMR. The desired perfluorofluoroformate (G') was obtained with about 96% yield.

Example 2 g Hydrolysis of Perfluoroformate (G')

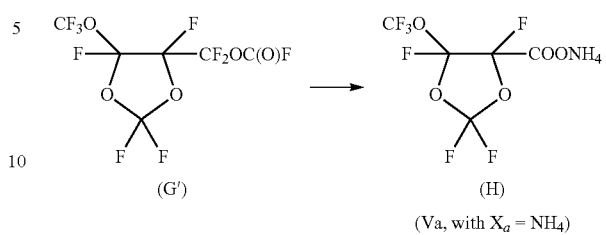

Same procedure as detailed in example 2d was followed.

Determination of Surface Tension of Aqueous Solution of Compounds Va and VIIa (with $X_a$=$NH_4$)

Surface tension measurements have been carried out on diluted solutions of ammonium salts of compounds (Va) and (VIIa) in water at a temperature of 25° C., using a LAUDA TE1C tensiometer equipped with a Pt ring; raw data have been worked up with Huh-Mason technique. For comparison purposes, surface tension has been also determined in same conditions on water solution of ammonium perfluorooctanoate (APFO). A sketch of the surface tension (in mN/m) as a function of concentration (in g/l) for compounds Va, VIIa and APFO is given in FIG. 4.

Simulation Using Density Functional Theory for Prediction of Biopersistence Behaviour of Compound Va Using density functional theory, minimum energy conformational structure of carboxylated anion of compound (Va) either in vacuum or in aqueous solution have been determined; in particular, volume and surface of the molecule in solution, solvatation free energy, length of main chain of the molecule, vibrational entropy, equivalent diameter, electrical charges at the oxygen and carbon atoms of the carboxylic groups, dipole momentum have been determined.

Structural and energetic data have been also calculated as above described for several fluorosurfactants such as perfluorooctanoate and other compounds having catenary oxygen atoms, for which biopersistence data were available, So as to establish appropriate correlations among said data and biopersistence profile. In particular, the ratio between solvatation free energy and the length of the molecule has been found to directly correlate to the fraction (%) of compound eliminated from a living animal in rats after 96 hours from administration, as determined by urine analysis.

On the basis of said relation, it has been possible to determine a recovery/elimination for cyclic compound of formula (Va) exceeding 95% after 96 hours from administration, while only 5% are expected to be rejected from living body from similar calculations from perfluorooctanoate. These data well demonstrate that the cyclic compounds of the invention indeed possess a more favourable biopersistence profile over traditional fluorosurfactants.

Blood and Urine Levels and Pharmacokinetic Parameters of Compounds Va and VIIa ($X_a$=$NH_4$)

Compound Va and VIIa ($X_a$=$NH_4$) were administered by single oral route (gavage) three male Wistar (SPF-bred) rats at dose levels of about 70 μmol/kg of dry ammonium salt, corresponding to the 21.2 mg/kg for compound Va and 19.9 mg/kg for compound VIIa. Blood sampling occurred 15 minutes before administration, at 4, 8, 12, 24, 72 and 168 hours after administration. For compound Va, maximal plasma concentrations ($C_{max}$) was observed at 4 h ($t_{max}$) with a reliable plasma half life of 3.1-4.5 hours after oral administration. For compound VIIa, maximal plasma concentrations ($C_{max}$) was also observed at 4 h ($t_{max}$) with a reliable plasma half life of 8.0-8.9 hours. The PK parameters of these compounds after single oral (gavage) administration to male rats are summarized in the table below:

TABLE 1

| Parameter | | Va ($X_a$ = $NH_4$) | VIIa ($X_a$ = $NH_4$) |
|---|---|---|---|
| Dose | [mg/g] | 21.2 | 19.9 |
| | | Males group (plasma) | |
| $C_{max}$ | [ng/mL] | 22997, 14997, 24345 | 11258, 14767, 18878 |
| $t_{max}$ | [h] | 4, 4, 4 | 4, 4, 4 |
| $AUC_{0-t}$ | [ng · h/mL] | 135856, 68016, 118024 | 47070, 114562, 135608 |
| $AUC_{inf.}$ | [ng · h/mL] | 136026, 68289, 121185 | 47137, 115916, 137788 |
| $t_{1/2, z}$ | [h] | 4.5, 3.1, 4.0 | 4.8, 8.0, 8.9 | data relative to the three animals dosed.

Individual and mean urine levels in rats, after single oral administration, resulted in urinary half lives of 9, 13, 10 hours with a recovery of 97-107% at 168 hours after treatment for compound VIIa; compound Va reported urinary half lives of 15, 11 and 28 hours with a recovery of 80-83% at 168 hours after treatment.

Compound XIII was dosed by single oral administration to 3 male Wistar rats at the dose of 73 umol/kg corresponding to 26.06 mg/kg. Blood sampling occurred at 15 minutes before administration, at 4, 8, 12, 24, 72 and 168 hours after administration. Urine samples were obtained at time intervals 0-12, 12-24, 24-72, 72-96, 96-168 hours after dosing. Plasma and urine concentration of XIII were determined by a validated analytical method. The maximum plasma concentration ($C_{max}$) was observed at 4 hours ($t_{max}$). Mean urinary recovery in 168 hours after treatment was around 82%.

Results of plasma concentrations for compound VIIa ($X_a$=$NH_4$), Va ($X_a$=$NH_4$), XIII ($X_a$=$NH_4$) and APFO as a function of time are sketched in FIG. 5. This graph depicts ratio $C/C_{max}$ for compound Va ($X_a$=$NH_4$) (●) compound VIIa ($X_a$=$NH_4$) (○), for compound XIII ($X_a$=$NH_4$) (□) and APFO (▲), with C=instantaneous plasma concentration and $C_{max}$=maximum plasma concentration, as a function of time (in hours).

Experimental data indicate significantly faster elimination of compound Va, VIIa and XIII ($X_a$=$NH_4$) from blood after single oral administration than what observed for APFO. Recoveries from urines for all the 3 compounds exceeded always 80% after 96 and 168 hours from treatment.

TGA Analyses of Compounds Va and VIIa ($X_a$=$NH_4$) and APFO as Comparison

FIG. 6 depicts the TGA traces as % wt loss as a function of temperature (in ° C.) for APFO (1), compound Va (2) and VIIa ($X_a$=$NH_4$) (3). These data well demonstrate that cyclic compounds are more volatile that perfluoroalkanoic acids and thus are expected to leave lower levels of residues in final parts obtained from dispersions containing the same.

Polymerization Example 3: PTFE Polymerization in the Presence of Compound Va ($X_a$=$NH_4$)

A polymerization reactor having a total volume of 100 cc equipped with a mechanical stirrer was charged with 60 cc of deionised water, 0.12 g of compound Va ($X_a$=$NH_4$) and 1.0 g of paraffin wax with softening point comprised 52° C. and 58° C. The reactor was evacuated and heated up to 70° C. The reactor was kept under mechanical stirring and loaded with gaseous TFE until reaching a pressure of 20 barg. The polymerization was initiated by a solution containing 0.5 mg of ammonium peroxodisulfate $(NH_4)_2S_2O_8$, (APS) and 9.6 mg of disuccinic acid peroxide (DSAP). Reaction pressure was maintained at set point of 20 barg by feeding gaseous TFE. The reaction temperature was increased until 80° C. with a rate of 0.5° C./min. After 80 min, feeding of TFE was interrupted, reactor was vented and cooled. A stable PTFE dispersion having a solid content of 20% wt was obtained; no coagulum was formed in the reactor during polymerization. The latex particle diameter was found to be 235 nm when measured by Laser Light Scattering (LLS).

Preparative Example 4

Synthesis of compound XIII (with $X_a$=$NH_4$)

Example 4a. Reaction Between perfluoro-5-methoxy-1,3-dioxole (MDO, (A) in Scheme Here Below) and Ethylene Glycol

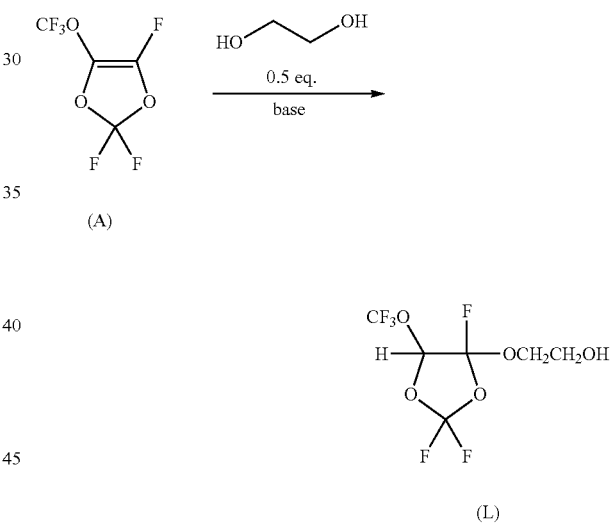

In a four necked roundbottomed glass reactor, equipped with magnetic stirrer, thermometer, condenser maintained at −75° C. (dry ice-isopropyl alcohol) and two addition funnels, 450 g of ethylene glycol were introduced; the reactor was cooled to 0° C. in an ice water bath; a solution of 11, 4 g (285 meq) of NaOH (s) and 60 ml of distilled water $H_2O$ was then added in half an hour. After a slight exothermicity, the mixture was heated to 80° C.; 150 g (714 mmoli) of MDO were thus slowly added. At the end of the addition, reaction mixture was stirred for another 2 hours. After cooling at 20° C., 250 ml of dichloromethane were added and resulting mixture was rinsed twice with brine. The organic (lower) phase was first dried over $MgSO_4$, filtered and then $CH_2Cl_2$ was evaporated. Isolated yield of compound (L) was found to be 74%.

Example 4b. Esterification of Alcohol Intermediate (L)

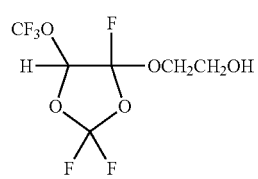

(L)

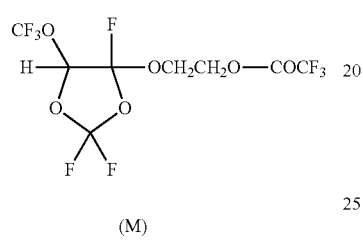

(M)

Alcohol intermediate (L) (184 mmol, 50 g) obtained from example 4a was made to react with $CF_3COF$ (200 mmol, 23.2 g) in 150 ml of A113 at T=0° C. Solvent and unreacted $CF_3COF$ were removed by distillation at 40° C./600 mm Hg.

Example 4c. Fluorination of Ester (M)

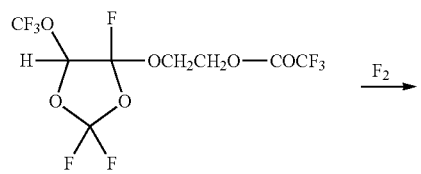

(M)

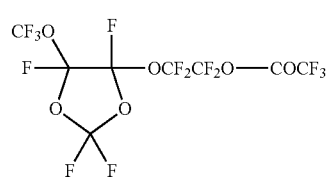

(N)

Ester (M) was diluted in A113 (150 ml) and fluorinated with a mixture $F_2/N_2$ (20/80) at a temperature of 0 to 30° C. Reaction was monitored by gas chromatography. Once fluorination was completed, residual $F_2$ was vented by bubbling a flow of nitrogen. Perfluoroester (N) was recovered after removal of solvent by fractional distillation.

Example 4d. Hydrolysis of Perfluoroester (N)

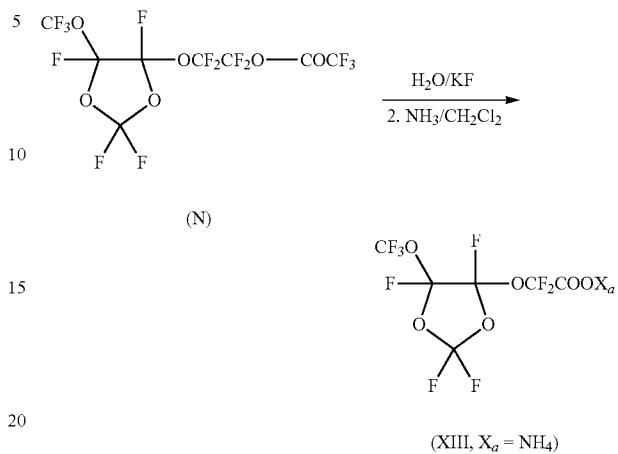

(XIII, $X_a$ = $NH_4$)

Perfluorinated ester (N) was hydrolyzed in water at 0° C., yielding the corresponding acid with quantitative yield. Evolved HF was neutralized with 1.5 mol eq. of KF, yielding solid $KHF_2$, which was separated by filtration. After removal of solvent, the free acid (XIII, $X_a$=H) and $CF_3COOH$ (b.p.=72° C.) were separated from each other by fractional distillation.

Acid (XIII, $X_a$=H) was solubilised in $CH_2Cl_2$ (200 ml); gaseous $NH_3$ was then bubbled in said solution; ammonium salt (XIII, $X_a$=$NH_4$) was then recovered with a yield of 75% moles (with respect to alcohol intermediate (L)). The thermogravimetric analysis (TGA) in air pointed out a weight decrease of 10% at 159° C. and of 50% at 191° C. FIG. 7 depicts the $^{19}$F-NMR spectrum recorded on ammonium salt (XIII, $X_a$=$NH_4$).

Example 4e. Fluoroformate Preparation from of Alcohol Intermediate (L)

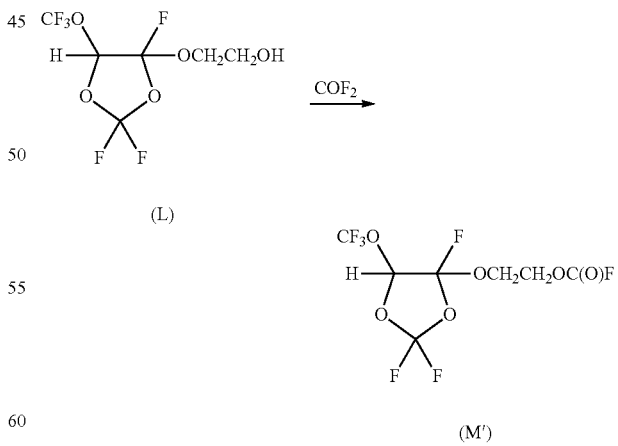

(M')

In a 500 ml stainless steel reactor equipped with mechanic stirrer, gas inlet, gas outlet, a thermocouple to check the internal temperature, and external cooling bath, 393 g of an alcohol of the above formula (L) and 92 g of powdered NaF were introduced and the external temperature set at 15° C.

Then, COF$_2$ (6.0 Nl/h obtained by reaction between 7.0 Nl/h of CO and 6.0 Nl/h of F$_2$) diluted with 2.0 Nl/h of He were introduced into the reactor while keeping reaction medium under vigorous stirring. The off-gases were analysed by a G.C. system to evaluate COF$_2$ conversion. After 6.75 hours feeding was stopped and crude mixture was filtered to separate inorganic salts. The liquid product was analyzed by $^{19}$F NMR showing an almost quantitative conversion of the starting alcohol and selectivity in the desired fluoroformate (M').

Example 4f. Fluorination of Fluoroformate (M')

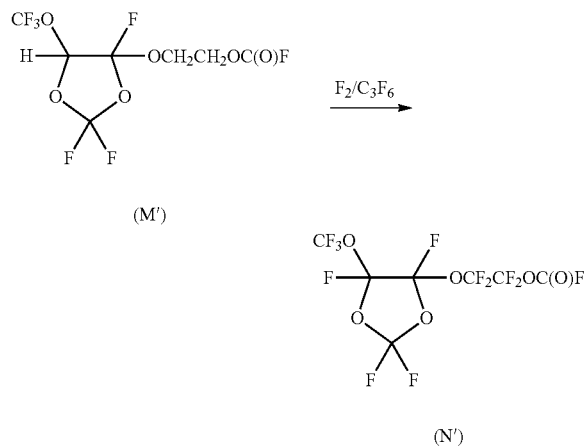

In a 500 ml stainless steel reactor equipped with mechanic stirrer, two gas inlets, one gas outlet, a thermocouple to check the internal temperature, and external cooling bath, 278 g of a fluoroformate of the above formula (M') were loaded and the external temperature set at 0° C. Then, two different stream of gases were introduced by the inlets into the reactor kept under vigorous stirring: F$_2$ (2, 3 Nl/h) diluted with 4.5 Nl/h of He, and C$_3$F$_6$ (0.3 Nl/h) diluted with 1.5 Nl/h of He. The off-gases went through a NaF trap and analyzed by GC to evaluate F$_2$ conversion and thus estimate the C—H to C—F conversion. The internal temperature remained constant at +5° C. After 57 hours, the internal temperature fell quickly from 5° C. to 0° C., and no additional F$_2$ conversion was observed. The feeding was stopped and the residual HF was removed by inert gas. The crude mixture was collected and analyzed by GC and $^{19}$F NMR. The desired perfluorofluoroformate (N') was obtained with a roughly 95% yield.

Example 4 g. Hydrolysis of Perfluoroformate (N')

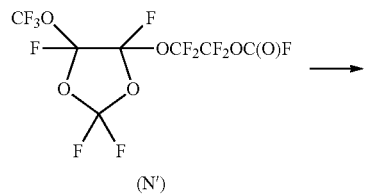

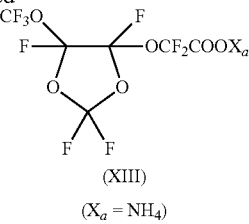

Same procedure as detailed in step 4d. was followed.

Determination of Surface Tension of Aqueous Solution of Compound XIII (With X$_a$=NH$_4$)

Surface tension measurements have been carried out on diluted solutions of ammonium salts of compound (XIII) as detailed above for (Va) and (VIIa). A sketch of the surface tension (in mN/m) as a function of concentration (in g/l) for compound (XIII) is given in FIG. 4.

TGA Analyses of Compounds XIIIa (X$_a$=NH$_4$) and APFO as Comparison

FIG. 8 depicts the TGA traces as % wt loss as a function of temperature (in ° C.) for APFO (1) and compound XIII (X$_a$=NH$_4$) (2). These data well demonstrate that cyclic compound is more volatile that perfluoroalkanoic acids, possibly via decarboxylation phenomena and thus is expected to leave lower levels of residues in final parts obtained from dispersions containing the same.

Further TGA isothermal scans under vacuum have been carried out on compound XIII (X$_a$=NH$_4$) at T=150 and 180° C., for evaluating decarboxylation kinetic; these scans are provided in FIG. 9, wherein in abscissa time (in minutes) is given, while other axis provides with the % of weight with respect to initial weight. GC coupled with mass spectrometry has enabled identifying in cyclic C$_5$O$_4$F$_9$H (i.e. corresponding decarboxylated compound) largely prevailing volatile material detected.

Polymerization Example 5:PTFE Polymerization in the Presence of Compound XIII (X$_a$=NH$_4$) and Recovery of Compound XIII (X$_a$=NH$_4$) by Ion Exchange A polymerization reactor having a total volume of 5000 ml equipped with a mechanical stirrer (500 rpm) was charged with 3 l of deionised water, heated at 60° C. and further loaded with 60 g of a 10% wt aqueous solution of compound XIII (X$_a$=NH$_4$) and 60 g of paraffin wax with softening point comprised 52° C. and 58° C. The reactor was evacuated and heated up to 70° C. The reactor was kept under mechanical stirring and loaded with gaseous TFE until reaching a pressure of 20 barg. The polymerization was initiated by introducing 30 ml solution containing 4 g/l of ammonium peroxodisulfate (NH$_4$)$_2$S$_2$O$_3$ (APS) and bringing temperature set point at 80° C. Reaction pressure was maintained at set point of 20 barg by feeding gaseous TFE. After having fed 1450 g of TFE, reactor was vented and cooled. A stable PTFE dispersion having a solid content of about 32% wt was obtained; no coagulum was formed in the reactor during polymerization. The latex particle diameter was found to be 230 nm when measured by Laser Light Scattering (LLS).

PTFE dispersion obtained as above detailed was stabilized by addition of 4.5% wt. (based on solids) of Tergitol® TMN 100× non-ionic surfactant. The dispersion was diluted to 9% wt. of solids and purified by treatment with Amberjet® 44000H anion exchange resins. The purified dispersion was found to contain less than 5 ppm of compound XIII (based on solids). No coagulum was formed during purification process.

Polymerization Example 6: TFE/Perfluoropropylvinyl Ether Copolymerization in the Presence of Compound VIIa ($X_a$=$NH_4$) and a Perfluoropolyether Surfactant A polymerization reactor having a total volume of 5000 ml equipped with a mechanical stirrer (470 rpm) was charged with 2550 g of deionized water, heated at 60° C. and further loaded with 150 g of a 5% wt aqueous solution of compound XIII ($X_a$=$NH_4$) and 200 g of a 1 wt aqueous solution of dicarboxylic perfluoropolyether acid ammonium salt of formula: $X_a$OOC—$CF_2O$—($CF_2O)_n$($CF_2CF_2O)_m$—$CF_2$—COO$X_a$ ($X_a$=$NH_4$, n, m being such that average molecular weight is 1800. The reactor was evacuated and heated up to 80° C. The reactor was kept under mechanical stirring and loaded with gaseous TFE until reaching a pressure of 20 barg, and initial charge of 20 g. of perfluoropropylvinylether (PPVE). The polymerization was initiated by introducing 35 ml solution containing 6 g/l of ammonium peroxodisulfate ($NH_4)_2S_2O_8$ (APS) and bringing temperature set point at 80° C. Reaction pressure was maintained at set point of 20 barg by feeding gaseous TFE. After having fed 100 g of TFE, additional perfluoropropylvinylether (PPVE) was fed in 5 subsequent amounts corresponding to a total load of 45 g. After having fed 1300 g of TFE, reactor was vented and cooled. A stable TFE/PPVE copolymer dispersion having a solid content of about 30% wt was obtained; no coagulum was formed in the reactor during polymerization. The latex particle diameter was found to be 97 nm when measured by Laser Light Scattering (LLS).

Polymerization Example 7: TFE Polymerization in the Presence of Compound XIIIa ($X_a$=$NH_4$) and Subsequent Upconcentration by Clouding A polymerization reactor with a total volume of 5 l equipped with an impeller agitator was charged with 3 l deionised water. The oxygen free reactor was heated up to 65° C. and the agitation system was set to 500 rpm. The reactor was charged with 60 g of paraffin wax, 9 g of compound (XIII, with $X_a$=$NH_4$), and with TFE to a pressure of 20 barg. The polymerization was initiated by 30 cc of a solution composed by 120 mg of ammonium peroxodisulfate ($NH_4)_2S_2O_8$(APS) and 15 mg of Mohr Salt ($NH_4)_2Fe(SO_4)_26H_2O$. As the reaction started, the reaction pressure of 20 barg was maintained by the feeding of TFE into the gas fase. The reaction temperature was increased until 80° C. After 130 min the feeding of 1600 g of TFE was completed, the monomer valves were closed and the stirring stopped. The reactor was depressurized, vented and cooled. The so obtained polymer dispersion was stable and had a solid content of 33% w/w, no coagulum was detected inside the reactor. The latex particle diameter was 200 nm according to the Laser Light Scattering (LLS) and using DSC analysis the melting point first fusion was 335° C. and the heat of crystallization was −42 J/g. Said dispersion was up-concentrated by clouding in a pyrex reactor obtaining a final composition of 74.3% w/w and then formulated to obtain a sample of 600 g composed by 60% PTFE, 5.8% Triton® X-100 non ionic emulsifier and having the following properties: pH=10.7; viscosity (20° C.)=31.5 cP; viscosity (35° C.)=22.5 cP; conductivity=1132 mS/cm; shear stress stability (61° C.)=627 sec.

A comparative dispersion polymerized in the same way but using APFO as surfactant usually has properties included in the following range: PTFE=59-61%; Triton® X-100 emulsifier=5-7%; pH=9.5-11; viscosity (20° C.)=35 cP max; viscosity (35° C.)=50 cP max; conductivity=800-1300 mS/cm; shear stress stability (61° C.)=300-350 sec.

Polymerization Example 8: TFE Polymerization in the Presence of Compound XIIIa ($X_a$=$NH_4$) and Recovery of Polymer Thereof as Dry Powder Step 8a-Polymerization A polymerization reactor with a total volume of 5 l equipped with an impeller agitator was charged with 3 l deionised water. The oxygen free reactor was heated up to 70° C. and the agitation system was set to 500 rpm. The reactor was charged with 60 g of paraffin wax, 9 g of compound (XIII, with $X_a$=$NH_4$) of which 5.5 g distributed during the reaction, and with TFE to a pressure of 20 barg. The polymerization was initiated by 16 cc of a solution composed by 8 mg of ($NH_4)_2S_2O_8$ (APS) and 160 mg of disuccinic acid peroxide (DSAP). As the reaction started, the reaction pressure of 20 barg was maintained by the feeding of TFE into the gas phase. The reaction temperature was increased until 85° C. After 146 min the feeding of 1400 g of TFE was completed, the monomer valves were closed and the stirring stopped. The reactor was depressurized, vented and cooled. The so obtained polymer dispersion was stable and had a solid content of 29% w/w, no coagulum was detected inside the reactor. The latex particle diameter was 227 nm according to the Laser Light Scattering (LLS) and using DSC analysis the melting point first fusion was 338.4° C. and the heat of crystallization was −33.3 J/g.

Step 8b—Product Recovery as Dry Powder

The dispersion from step 8a was coagulated, washed and dried for 32 hours respectively at 140-160-180° C. According to GC analysis, the residual amount of compound (XIII) on dried powder was <20 ppm (limit of the analysis) in all the three cases.

Recovery Example 9: Adsorption/Desorption of Compound XIII ($X_a$=$NH_4$) on Ion Exchange Resins 4 gr of anionic exchange resin Dowex MSA, previously washed with demineralized water and drained, were contacted for 24 hours with 100 gr of a 1.3% w/w solution of compound (XIII, with $X_a$=$NH_4$). The resin saturation was found to be 24.5%.

The so obtained exhausted/saturated resin was washed under vacuum with demineralized water and drained. A part of this resin, 3.5 gr, after a further rinsing step (30 ml of water), was extracted with 60 ml of a solution composed by 70% of methanol and 30% of sulphuric acid, and washed again with 30 ml of water. The acid solution and the rinsing water were collected, diluted with water, saponificated with NaOH until pH=11.2 and finally diluted with water until 250 gr. GC analysis showed a recovery of compound (XIII) of 70%.

Polymerization Example 10: Manufacture of a PVDF Latex in the Presence of Mixture of Surfactant A reactor having an inner volume of 7.57 l was charged with 5241 g of deionized water, 134 g of 10% w/w aqueous solution of compound XIII ($X_a$=$NH_4$), and 5.4 mg of dicarboxylic perfluoropolyether acid ammonium salt of formula: $X_a$OOC—$CF_2$O—($CF_2$O)$_n$($CF_2CF_2$O)$_m$—$CF_2$—COOX$_a$ ($X_a$=$NH_4$, n, m being such that average molecular weight is 1800), and 4 g of wax. The reactor was heated to 100° C. and vented for 2 min. The temperature was increased to 122.5° C. and the reactor was pressurized with vinyledene fluoride (VDF) to 650 psi. 24.4 mL of di-tert-butyl peroxide were added to the reactor to initiate polymerization, and the pressure was maintained at 650 psi throughout polymerization. Upon reaching target conversion (2298 g of consumed monomer), the monomer feed and agitation were stopped, the reactor was cooled, and the polymer latex was collected from the reactor, having a solid content of 28% wt and an average particle size of dispersed polymer particles of 282 nm. The latex was filtered to collect eventual coagulum and the reactor was inspected to determine the amount of build-up (e.g. polymer stuck onto the agitation blade and reactor walls).

Polymerization Example 11: TFE/Perfluoropropylvinyl Ether Copolymerization in the Presence of Compound VIIa ($X_a$=$NH_4$) and a Perfluoropolyether Surfactant Previously Mixed Under the Form of a Microemulsion Step 10 a—Manufacture of a Stable Dispersion in Water of Compound XIII (with $X_a$=$NH_4$) and Further Fluorinated Emulsifier In a glass flask, equipped with a stirrer, were mixed under mild stirring 24.00 g of a surfactant of formula XIII (with $X_a$=$NH_4$), 24.00 g of demineralized $H_2O$; 12.00 g of a dicarboxylic perfluoropolyether acid of formula: HOOC—$CF_2$O—($CF_2$O)$_n$($CF_2CF_2$O)$_m$—$CF_2$—COON (m, m being such that average molecular weight is 1800). The system spontaneously formed a microemulsion, which appears as a limpid, thermodynamically stable dispersion. The droplets average diameter was found to be 11.7 nm when measured by Laser Light Scattering (LLS).

Step 10 b—Polymerization of tetrafluoroethylene (TFE) and Perfluoropropylvinylether (PPVE)

A reactor having inner volume of 5 l was loaded with 3.0 l of water and 33 ml of above mentioned microemulsion. Temperature was raised to 75° C.; reactor was loaded with 50 g of perfluoropropylvinylether and pressurized with ethane until increase of 470 mbar, and finally pressurized with TFE at a set-point pressure of 20 bar. Polymerization was initiated by addition of ammonium persulfate (0.48 g introduced at the beginning, 0.30 g further injected in five portions in combination with further additions of perfluoropropyl vinylether. Polymerization was pursued until reaching overall monomers consumption of 1500 g after 76 min. A latex having a solids content of 31% wt and comprising particles having an average diameter (as determined by LLS) of 60 nm of a TFE/PPVE copolymer (PPVE: 3.1% wt) having a MFI of 30 g/10 min (372° C./5 kg, measured according to ASTM D 1238), a melting point of 305.7° C. and a heat of crystallization of −27.3 J/g (measured according to ASTM D 3418).

The invention claimed is:

1. A cyclic fluorocompound complying with formula (VIII) here below:

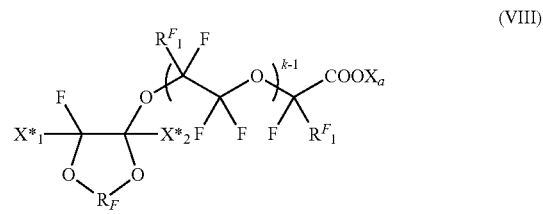

(VIII)

wherein $R_F$ is a divalent fluorinated $C_{1-3}$ bridging group; $X_a$ is H, a monovalent metal or an ammonium group of formula —N(R'$_n$)$_4$, wherein R'$_n$, equal or different at each occurrence, represents a hydrogen atom or a C1-6 hydrocarbon group; $X^*_1$, $X^*_2$ equal to or different from each other are independently a fluorine atom, —R'$_f$ or —OR'$_f$, wherein R'$_f$ is a $C_{1-3}$ perfluoroalkyl group; $R^F_1$ is F or $CF_3$; k is an integer from 1 to 3.

2. The cyclic fluorocompound of claim 1, complying with formula (XIII) here below:

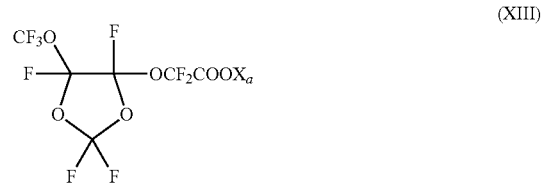

(XIII)

wherein $X_a$ has the same meaning as in claim 1.

3. A fluoropolymer dispersion comprising at least one cyclic fluorocompound according to claim 1.

4. A fluoropolymer dispersion comprising at least one cyclic fluorocompound according to claim 2.

* * * * *